United States Patent
Dehgan et al.

(10) Patent No.: US 12,064,763 B2
(45) Date of Patent: Aug. 20, 2024

(54) SYSTEMS AND METHODS FOR DETERMINING PRESENCE AND/OR CHARACTERISTICS OF TARGET ANALYTES IN A SAMPLE

(71) Applicant: Conservation X Labs, Inc, Northwest, WA (US)

(72) Inventors: Alex Dehgan, Washington, WA (US); Paul Bunje, Los Angeles, CA (US); Hallie Holmes, Seattle, WA (US); David Baisch, Seattle, WA (US); Cifeng Fang, Redmond, WA (US); Gareth Fotouhi, Seattle, WA (US); Misa Winters, Brier, WA (US); Sam Kelly, Arlington, VI (US); Brad Zamft, New York, NY (US)

(73) Assignee: Conservation X Labs, Inc

( * ) Notice: Subject to any disclaimer, the term of this patent is extended or adjusted under 35 U.S.C. 154(b) by 0 days.

(21) Appl. No.: 17/770,643

(22) PCT Filed: Oct. 21, 2020

(86) PCT No.: PCT/US2020/056727
§ 371 (c)(1),
(2) Date: Apr. 21, 2022

(87) PCT Pub. No.: WO2021/081136
PCT Pub. Date: Apr. 29, 2021

(65) Prior Publication Data
US 2022/0347682 A1 Nov. 3, 2022

Related U.S. Application Data

(60) Provisional application No. 62/923,637, filed on Oct. 21, 2019.

(51) Int. Cl.
*B01L 3/00* (2006.01)
*B01L 7/00* (2006.01)
(Continued)

(52) U.S. Cl.
CPC ....... *B01L 3/502715* (2013.01); *B01L 3/5085* (2013.01); *B01L 7/52* (2013.01);
(Continued)

(58) Field of Classification Search
CPC ....... B01L 3/502715; B01L 2300/0864; B01L 2200/0684
(Continued)

(56) References Cited

U.S. PATENT DOCUMENTS 4,314,968 A * 2/1982 Guigan .............. G01N 33/5302
436/501
4,522,622 A * 6/1985 Peery .................... A61M 5/282
604/185
(Continued)

FOREIGN PATENT DOCUMENTS

WO   2014100725 A1   6/2014
WO   2019055135 A1   3/2019

OTHER PUBLICATIONS

International Search Report and Written Opinion received for International PCT Application No. PCT/US2020/056727, mailed on Feb. 8, 2021, 17 Pages.
(Continued)

*Primary Examiner* — Natalia Levkovich
(74) *Attorney, Agent, or Firm* — EcoTech Law Group, P.C.

(57) ABSTRACT

A cartridge for providing a target analyte for detection is described. One such exemplar cartridge includes a base portion including: (1) a receiving area disposed at or near a center region of the base portion; (2) multiple reaction wells
(Continued)

disposed outside the center region or radially disposed at or near a perimeter of the base portion; and (3) multiple connecting tracks that substantially linearly extend from a region at or proximate to the receiving area to the multiple reaction wells and designed to convey a sample including the target analyte from the receiving area to the multiple reaction wells, each of which are configured to transform the sample to a detectable sample.

Systems and methods of reacting and detecting the sample including the target analyte are also described.

17 Claims, 18 Drawing Sheets

(51) Int. Cl.
    *G01N 21/03*    (2006.01)
    *G01N 21/25*    (2006.01)
    *G01N 33/53*    (2006.01)
    *G01N 35/00*    (2006.01)

(52) U.S. Cl.
    CPC ....... *G01N 21/0332* (2013.01); *G01N 21/253* (2013.01); *G01N 33/53* (2013.01); *B01L 2200/0684* (2013.01); *B01L 2300/0654* (2013.01); *B01L 2300/0816* (2013.01); *B01L 2300/0864* (2013.01); *G01N 2035/00376* (2013.01)

(58) Field of Classification Search
    USPC .................................................. 422/554, 552
    See application file for complete search history.

(56) References Cited

U.S. PATENT DOCUMENTS

| | | |
|---|---|---|
| 2008/0057544 A1 | 3/2008 | Lem et al. |
| 2013/0004952 A1 | 3/2013 | Castagna et al. |
| 2013/0220931 A1 | 8/2013 | Petersen et al. |
| 2015/0140562 A1 | 5/2015 | Conoci et al. |

OTHER PUBLICATIONS

Office Action received for Canadian Patent Application No. 3154966, pp. 8.

\* cited by examiner

SYSTEMS AND METHODS FOR DETERMINING PRESENCE AND/OR CHARACTERISTICS OF TARGET ANALYTES IN A SAMPLE

RELATED APPLICATION

This application is a National Stage Application of PCT/US20/56727 filed on Oct. 21, 2020, which claims priority to a provisional patent application No. 62/923,637 which was filed on Oct. 21, 2019, which are incorporated herein by reference for all purposes.

FIELD

The present arrangements and teachings relate to portable and hand-held devices, and related methods, for testing samples containing one or more target analytes (e.g., viruses such as severe acute respiratory syndrome coronavirus 2, harmful bacteria and chemical constituents of interest, and RNA, DNA and/or protein for purposes of species identification). More specifically, the present arrangements and teachings relate to a device, and methods relating thereto, that use a lysing chamber and/or a reaction/detection chamber, each connected to the same energy source, electronic user-interface and processor, for testing for presence and/or characteristics of the target analytes using an optical detection system.

BACKGROUND

Testing samples containing one or more target analytes, and in particular, biosamples with one more target nucleic acids, has been a staple of biology laboratories for many decades. The advent of quantitative real-time PCR (qPCR) made the identification of and measurement of genetic targets accessible and practical for a greater number of analytical tests and applications. This allows for the presence and/or characteristics of a target to be monitored through a reaction driven by external thermal energy input (e.g., thermomechanical energy). A computer-controlled reaction chamber is used to precisely control the reaction temperature for a desired method. Optical sensors, placed in a separate detection chamber, are used to measure the signal emitted by target analytes during the reaction method.

Conventional systems and methods have been used in professional laboratory settings, wherein sample preparation and data analysis has been performed by experts trained to use sophisticated equipment in laboratory settings that also provide access to various storage conditions for reaction materials (e.g., refrigerators) to practice these systems and methods. Demands for diagnostic testing in resource-limited areas that do not have access to such laboratory settings and personnel, however, remain. What is therefore needed are systems and methods that provide for sufficiently accurate reactions and diagnostic tests that determine presence and/or characteristics of one or more target analytes (including but not limited to biosamples having one more target nucleic acids or proteins) using an automated, sample-to-result methods, and, in turn, novel devices to practice such a methods, that may be performed by non-expert users and provide immediate results in the field.

SUMMARY

To this end, the present arrangements and teachings offer different types of systems, and methods relating thereto, that allow an automated, sample-to-result methods that may be performed by non-expert users and provide immediate results in the field.

In one aspect, the present arrangements provide cartridge designs for providing a sample including a target analyte for detection. One such exemplar cartridge design comprises a base portion including a receiving area, multiple reaction wells and multiple connection tracks, each of which defines a flow path between a region at or proximate to the receiving area and each of multiple reaction wells. In this configuration, the receiving area is disposed at or near a center region of the base portion. The multiple reaction wells are disposed outside the center region or radially disposed at or near a perimeter of the base portion. Further, multiple connecting tracks, which substantially linearly extend from a region at or proximate to the receiving area to the multiple reaction wells, are designed to convey a sample including the target analyte from the receiving area to the multiple reaction wells. Moreover, each of the reaction wells are configured to transform the sample to a detectable sample.

In a preferred arrangement of this exemplar cartridge design, a cap portion is provided. According to this design, certain structural features of the cap portion corresponds to that of the base portion. The cap portion, preferably, includes an inlet port disposed at a center cap region of the cap portion and multiple reaction well covers that are disposed outside the center cap region or radially disposed at or near a perimeter of the cap portion. Further, the cap portion may also include multiple connecting track covers that extend from the inlet port to the multiple reaction well covers. In an assembled state of the cartridge, the inlet port is disposed adjacent to the receiving area, the multiple reaction well covers are disposed adjacent to the multiple reaction wells, and the multiple connecting track covers are disposed adjacent to the multiple connecting tracks to define an enclosed flow path, or a channel, within the cartridge, for the sample.

In certain preferred embodiments, the base portion of the present arrangements further includes multiple securing features that are designed to secure therewithin an edge of the cap portion such that the cap portion is effectively secured to the base portion. The base portion, preferably, further still includes a supporting feature having disposed thereon the receiving area and multiple channel dividers. In this configuration, the multiple channel dividers are radially disposed around the receiving area such that multiple channel entry regions are defined therebetween for receiving the sample received at the receiving area.

In accordance with certain embodiments, the cap portion of the present arrangements further includes one or more vents designed to regulate flow of the sample into the multiple reaction wells. The cross-sectional area of the vent ranges from about 0.01 $mm^2$ to about 0.25 $mm^2$, and is preferably about 0.09 $mm^2$. One dimension of the inlet port may range from about 1 mm to about 5 mm and if the inlet port is of circular shape, then a diameter of the inlet port ranges from about 3.5 mm to about 3.8 mm. An exemplar volume held inside one of the multiple reaction wells may range from about 5 microliters to about 100 microliters.

The cartridge designs of the present teachings accounts for undergoing compression during operating conditions. To this end, in one exemplar design, the above-mentioned multiple reaction wells are part of multiple reaction well housings within the base portion. In this embodiment, each of the multiple reaction housings include a first compression resisting region and a second compression resisting region. Further, in connection with the cap portion, correspondingly, the multiple reaction well covers are part of multiple reaction cover housings, each of which includes a first compression region. Each of multiple connecting track covers include a second compression region. In an assembled state of the base portion and the cap portion, the first compression resisting region combines with the first compression region to form a first seal and the second compression resisting region combines with the second compression region to form a second seal. Further, in a compressed state of the cartridge, the first seal and the second seal effectively seal off the multiple reaction wells from ambient conditions and/or prevent evaporation during thermal processing. In certain preferred embodiment, said first seal of the present arrangements seals off one or more vents to prevent flow inside and/or outside one of said multiple reaction wells. A third compression region is, preferably, disposed on or near the inlet port of certain present arrangements, such that in a compressed state of the third compression region, the inlet port is sealed from ambient conditions.

To further facilitate compression of the cartridge, the cap portion is made from a compressible material so that it compresses as it encounters compression forces and the base portion is made from a rigid material to mechanically support the cartridge under compression. Along another line of design consideration, to facilitate optical detection of the detectable sample present inside each of the multiple reaction wells, the base portion and/or the cap portion are, preferably, made from an optically transparent material.

A base portion flow path, which is defined from the receiving area to each of the multiple reaction wells, may include one of the multiple channel entry regions, one of the multiple connecting tracks, and one of the multiple second compression resisting regions.

In certain preferred embodiments, multiple reaction wells of the present arrangements are non-linearly arranged (e.g., substantially circular arrangement) outside the center region of the base portion. In even more preferred embodiments, the base portion and the cap portion are of circular shape. In those instances where the multiple reaction wells are also of circular shape, a diameter of the reaction well may range from about 1 mm to about 4 mm.

The present cartridge arrangements may include an orientation key that extends from an edge of the base portion and away from the center region. The orientation key is designed to place the cartridge in a desired orientation that allows effective heating and/or detection of the sample including the target analyte inside each of the reaction wells. The orientation key provides a point of reference for the target analyte data collecting device to identify the position of each reaction well.

Inside the cartridge of the present arrangements, multiple flow paths are preferably designed. To accomplish this, multiple sidewalls, each extending from the base portion to the cap portion, are provided. In this configuration, the multiple sidewalls, the multiple connecting tracks and the multiple connecting track covers integrate to define multiple channels, each of which linearly extends, and thereby provides an enclosed flow path, from one of the multiple channel dividers to one of the multiple reaction wells. The sidewalls may be raised, from a base of the connecting track, by a height ranging from about 0.2 mm to about 3.0 mm. The resulting channel may linearly extend by a distance that ranges from about 2 mm to about 12 mm and may have a cross-sectional area that ranges from about 0.6 mm$^2$ to about 1.0 mm$^2$.

In another aspect, the present arrangements provides a reaction chamber for thermally activating multiple samples including a target analyte. One such exemplar reaction chamber includes a cartridge stage and a reaction heating block. Although this exemplar design and other variations thereof are described in terms of a cartridge, the present arrangements of the reaction chamber are not limited to being used with the cartridge designs described herein, and other cartridge designs that are not described herein may well be used in the present reaction chambers.

Regardless of the type of cartridge employed, the cartridge stage of the present reactor has defined therein an opening for receiving a cartridge. This opening is designed to have disposed therein multiple reaction wells, each of which holds the sample including the target analyte. The reaction heating block is disposed inside a housing that is proximate to the cartridge stage. Further, the reaction heating block has defined therein a heating block aperture that preferably aligns with the cartridge stage opening and that includes an inner heating surface of a curved profile, which conforms to a preferably curved profile of an outer surface of a side portion of the multiple reaction wells. As a result, upon direct contact of the inner heating surface with the outer surface of the side portion of the multiple reaction wells, the reaction heating block effectively thermally activates the multiple samples including the target analyte contained inside the multiple reaction wells. Stated another way, during an operative state of the reaction heating block, the cartridge is secured on the cartridge stage such that the curved profile of the inner heating surface conforms to the preferably curved profile of the outer surface of the side portion of the multiple reaction wells to effectively thermally activate multiple samples including the target analyte contained inside the multiple reaction wells.

Each of the cartridge stage opening and the reaction heating block is, preferably, of a non-linear shape. More preferably, each of the opening and the reaction heating block is of circular shape. In this embodiment, the reaction heating block has a diameter that ranges from about 10 mm to about 50 mm. Further, a diameter of the aperture ranges from about 3 mm to about 48 mm. Moreover, a height or a thickness of the reaction heating block has a value that ranges from about 1 mm to about 20 mm.

In certain preferred embodiments of the present arrangements, the reaction chamber includes multiple alignment ribs disposed inside the housing that are designed to receive the reaction heating block. In this configuration, the reaction heating block includes an outer heating surface such that the multiple alignment ribs are disposed around the reaction heating block and contact the outer heating surface to secure and prevent displacement of the reaction heating block.

The reaction chamber may further include a rigid, optically transparent film disposed adjacent to the reaction heating block. In this embodiment, the optically transparent film is designed to mechanically support the cartridge under compression. To facilitate compression, the reactor may include a compression module that during an operative state of the reaction chamber, compresses a cap portion of the cartridge, that is secured within the opening. The cap portion is designed to prevent escape of vapor from the multiple reaction wells and/or to prevent cross-contamination between the different multiple reaction wells. Moreover, placing the cap portion under compression further ensures preventing escape of vapor and cross-contamination between the different reaction wells.

In yet another aspect, the present arrangements provide optical detection assemblies for detecting at least one property of multiple samples including a target analyte. One such exemplar optical detection assembly includes a cartridge stage having defined therein an opening for receiving a cartridge that has defined therein multiple reaction wells. Each of these reaction wells is configured to hold the sample including the target analyte. This exemplar optical detection assembly also includes multiple, non-linearly arranged, excitation light sources and multiple, non-linearly arranged, photodetectors. The excitation sources are positioned adjacent to one side of or above the cartridge stage and designed to emit an incident light beam and the photodetectors also positioned adjacent to, but on the other side of or below the cartridge stage, is designed to detect a transmitted light beam. In this configuration, the position of each of the multiple excitation light sources longitudinally aligns with the position of a corresponding one of the multiple photodetectors. During an operative state of the multiple photodetectors, an incident light beam, generated at one of the multiple excitation light sources, extends longitudinally to strike and be transmitted through the sample including the target analyte in the multiple reaction wells. A resulting transmitted light beam propagates towards a corresponding one of the photodetectors. Upon the arrival of the transmitted light beam, at least one property of the target analyte is measured by the corresponding one of the multiple photodetectors. By way of example, at least one property of the transmitted light beam is intensity and/or fluorescence.

Although not necessary, the multiple excitation light sources are, preferably, arranged in a circular configuration and in corresponding fashion, the multiple photodetectors are also, preferably, arranged in the circular configuration. The multiple excitation light sources emit light at wavelengths having a peak intensity that ranges from about 320 nm to about 790 nm and, preferably, ranges from about 430 nm to about 510 nm. The multiple excitation light sources are at least one member selected from a group comprising light emitting diodes, lasers, and excited gas lamps. On the detection side, multiple photodetectors are at least one member chosen from a group comprising photodiodes, photoresistors, and complementary metal oxide sensors (CMOS).

The present optical assemblies may further include an excitation filter disposed between the multiple excitation light sources and the multiple reaction wells. The excitation filter blocks wavelengths greater than a band of excitation wavelengths and allows the band of excitation wavelengths to pass through. In an operative state of the excitation filter, the excitation wavelengths are incident upon the multiple reaction wells.

The present optical assemblies may further still include an emission filter disposed between the multiple reaction wells and the multiple photodetectors. The emission filter blocks wavelengths less than the band of excitation wavelengths and allows wavelengths greater than the band of excitation wavelengths to pass through the emission filter to produce multiple emission signals. In an operative state of the optical detection assembly, the multiple emission signals are detected by the multiple photodetectors. Preferably, the multiple emission signals are generated by a beam of light contacting the probes associated with a target analyte in a reaction well.

The emission filter and/or the excitation filter may be made from a glass or polymer substrate having a coating that provides for pass-through of desired wavelengths.

In numerous preferred embodiments, the present optical assemblies further include at least one member chosen from a group comprising excitation light source alignment key, compression module, aperture cover, and photodetector base.

According to certain preferred embodiments of the present arrangement, multiples of excitation light source alignment keys may be disposed adjacent to and around the multiple excitation light sources for aligning the multiple excitation light sources with the multiple reaction wells and the multiple photodetectors.

If a compression module for sealing the reaction wells is used, it is disposed between the excitation filter and the cartridge. In this arrangement, the compression module includes multiple light channels that align with the multiple excitation light sources and the multiple reaction wells and provides an optical path for passage of the band of excitation wavelengths and wavelengths greater than the band of excitation wavelengths to enter the multiple reaction wells.

If an aperture cover is used, it is disposed between the multiple reaction wells and the emission filter. The aperture cover has defined therein multiple crosstalk preventing apertures and in an installed configuration, it aligns with the multiple excitation light sources, the multiple reaction wells, and the multiple photodetectors, for preventing crosstalk between transmitted light from different multiple reaction wells.

Use of a photodetector base, aligned adjacent to and around the multiple photodetectors, also marks preferred embodiments of the present arrangements. The photodetector base has defined therein multiple base apertures that are configured to align the multiple photodetectors with the multiple reaction wells and the multiple excitation light sources.

The aperture cover may be made from an opaque material. Further, the multiple excitation light source alignment keys and/or the photodetector base may be made from an opaque polymer that is not auto fluorescent or excitable by light transmitted by the multiple excitation light sources.

The photodetector base may be of non-linear shape and has, non-linearly arranged, multiple base apertures defined therein. The position of each of the base apertures longitudinally aligns with position of a corresponding one of the multiple excitation light sources such that the transmitted beam of light propagating into one of the base apertures strikes the corresponding one of the multiple photodetectors.

In yet another aspect, the present arrangements provide target analyte data collecting devices. One such exemplar device includes a lysing chamber and a reaction chamber. The lysing chamber is configured for lysing a sample containing an analyte to produce a lysed sample. Further, the lysing chamber includes a lysing heating block that has defined therein a cavity region having an inner surface, which conforms to a shape of a lysing tube such that the cavity region is configured to receive the lysing tube containing the sample. The present teachings recognize that chemical reactions alone, in the absence of heating, produce a lysed sample. As a result, using a lysing heating block is an optional feature inside the lysing chamber.

Regardless of the approach used to produce a lysed sample, the reaction chamber is designed to thermally activate the lysed sample. The reaction chamber includes a non-linear-shaped reaction heating block having defined therein a heat block aperture, which includes an inner heating surface having a curved profile that conforms to a curved profile of an outer surface of side portions of multiple reaction wells disposed on a cartridge. When the cartridge is placed inside the reaction chamber to facilitate direct contact of the inner heating surface with the outer surface of the side portions of the multiple reaction wells, the heating block is designed to effectively thermally activate the lysed sample.

In certain preferred embodiments, the reaction chamber includes a core assembly portion and a handle portion. The core assembly portion includes the lysing chamber, the reaction chamber, and a separation that separates the lysing chamber from the reaction chamber. The handle portion includes an energy source coupled to the lysing heating block and the reaction heating block and configured to energize the lysing heating block and the reaction heating block. A printed circuit board, disposed inside the handle portion, is coupled to the energy source and has stored thereon programmable instructions for providing an output based on inputs received from the lysing chamber and/or the reaction chamber. Further, a user interface, disposed in the handle portion, is communicatively coupled to receive the output, based upon which the user interface designed to display useful information and/or instructions. In a most preferred configuration, core assembly portion and a handle portion are integrated into the target analyte data collecting device that is capable of being hand-held and portable for field use by a user. The user may be a non-technically trained user that implements various regimens pre-programmed on the target analyte data collecting device, preferably via a user interface connected to that device.

The lysing chamber and the reaction chamber are preferably not coupled to a cooling mechanism energized by the energy source. For example, when lysing or thermal activation is being carried out under isothermal conditions, the target analyte data collecting devices of the present arrangements do not rely upon, and operate independently of, a cooling mechanism energized by the energy source on the device.

The lysing chamber may further include a first temperature sensor and a first heater input, both of which are communicatively coupled to the printed circuit board (which has programmable instructions stored thereon for the first thermomechanical regimen). The first temperature sensor and the first heater input may also be communicatively coupled to the lysing heating block. Based upon these communicatively coupled arrangements and based upon the programmable instructions, the printed circuit board is capable of automating the first thermomechanical regimen in the lysing chamber.

Similarly, inside the reaction chamber, a second temperature sensor and a second heater input are provided. Both of the second temperature sensor and the second heater input are communicatively coupled to the printed circuit board (which has programmable instructions stored thereon for the first thermomechanical regimen) and communicatively coupled to the reaction heating block. Based upon these communicatively coupled arrangements and based upon the programmable instructions, the printed circuit board is capable of automating the second thermomechanical regimen in the reaction chamber.

The handle portion may have a length that ranges from about 50 mm to about 120 mm and may have a thickness that ranges from about 15 mm to about 35 mm. The core assembly portion may have a length that ranges from about 90 mm to about 120 mm and may have a thickness that ranges from about 40 mm to about 70 mm.

In certain preferred embodiments, the lysing heating block of the present arrangements is fitted with a first heater input for energizing, using a first thermomechanical regimen, the sample to prepare the lysed sample. In this arrangement, the first thermomechanical regimen is stored on the printed circuit board. A temperature sensor may also be coupled to the lysing heating block and/or the printed circuit board.

The reaction heating block is, preferably, fitted with a second heater input for energizing, using a second thermomechanical regimen, the lysed sample to prepare the detectable sample. In this arrangement, the second thermomechanical regimen is stored on the printed circuit board. A temperature sensor may also be coupled to the reaction heating block and/or the printed circuit board.

In the target analyte data collecting devices of the present arrangements, the multiple photodetectors, present inside the reaction chamber, may be configured to detect an emission signal generated by a probe in the detectable sample. The multiple photodetectors, if arranged to be communicatively coupled to the printed circuit board inside the handle portion, then during an operative state of the target analyte data collecting device, the emission signal generated by the probe is conveyed to the printed circuit board inside the handle portion.

In yet another aspect, the present arrangements provide reaction chamber for thermally activating multiple samples containing a target analyte. One such exemplar of the reaction chamber includes a reaction assembly and a detection assembly.

The reaction assembly includes a cartridge stage and a reaction heating block. The cartridge stage has defined therein an opening for receiving a cartridge, which has disposed thereon multiple reaction wells. The reaction block is disposed adjacent to the cartridge stage and has defined therein a heating block aperture. An inner heating surface of the heating block aperture has a curved profile designed to conform to a curved profile of an outer surface of a side portion of the multiple reaction wells. Upon direct contact of the inner heating surface with the outer surface of the side portion of the multiple reaction wells, the heating block effectively thermally activates the analyte contained inside multiple reaction wells.

The optical detection assembly includes multiple, non-linearly arranged, excitation light sources and multiple, non-linearly arranged, photodetectors. The excitation light sources are disposed adjacent to the cartridge stage and designed to emit an incident light beam. The multiple photodetectors are also disposed adjacent to the cartridge stage but designed to detect a transmitted light beam. In this configuration, the positions of each of the multiple excitation light sources, a corresponding one of the multiple reaction wells, and the corresponding one of the multiple photodetectors longitudinally align with each other. During an operative state of the reaction chamber, multiple incident light beams, generated at one of the multiple excitation light sources, each extend longitudinally to strike and be transmitted through the corresponding one of the multiple reaction wells and generate the transmitted light beam, at least one property of which is measured by the corresponding one of the multiple photodetectors.

In certain preferred configurations of the present arrangements, the reaction assembly and the optical detection assembly extend in an overlapping longitudinal space. In certain other preferred embodiments, the reaction assembly is disposed within certain components of the optical detection assembly.

The present reaction chamber for thermally activating may further include a compression module for compressing a cap portion of the cartridge. The compression module has defined therein multiple light channels, each of which provides an optical path to a light beam generated at one of the multiple excitation light sources. During an operative state of the reaction chamber, the incident light beam is transmitted through a corresponding one of the light channels to strike the corresponding one of the multiple reaction wells.

In one aspect, the present teachings provide methods of detecting a presence and/or a characteristic of a target analyte. One such exemplar method, preferably, begins with a step of obtaining a cartridge including a base portion and a cap portion. The cap portion includes an inlet port and the base portion including multiple wells. Further, the inlet port and multiple reaction wells are communicatively coupled such that a sample containing the target analyte received at the inlet port is distributed to the multiple reaction wells. The exemplar method then proceeds to a step of introducing, into the inlet port, the sample containing the target analyte to form a loaded cartridge.

Next, a placing step involves placing the loaded cartridge inside a reaction chamber. Then, a compressing step includes compressing the loaded cartridge to form a compressed cartridge such that the multiple reaction wells are sealed to form sealed multiple reaction wells. The exemplar method then performs a commencing step of heat treating the sample containing the target analyte in the sealed multiple reaction wells such that from no amount to a substantially reduced amount of evaporation of the sample escapes the sealed multiple reaction wells.

In certain preferred implementations of the present teachings, the exemplar method further includes equally distributing, during the introducing, the sample containing the target analyte inside the multiple wells. The exemplar method may further include orienting, prior to compressing, the cartridge using an orientation key disposed on the cartridge. In this step, the orientation key serves as a point of reference that positions each of the multiple reaction wells at a predefined location. In one implementation, the commencing step of the present teachings includes contacting a reaction heating block with the multiple reaction wells.

The exemplar method of detecting a presence and/or a characteristic of a target analyte further includes, prior to the step of introducing, preloading reaction materials in the multiple reaction wells to form a pre-loaded cartridge. In this step of preloading, the reaction materials is at least one member chosen from a group comprising reagent, buffer, and probe. The exemplar method may further include, after the step of preloading, a step of lyophilizing the reaction materials in the multiple reaction wells. In an alternate approach, the exemplar method includes a step of lyophilizing and/or freeze drying any one of the reaction materials chosen from a group comprising reagent, buffer and probe to form a bead of the reaction material. According to this approach, next a step of preloading includes preloading each of said multiple reaction wells with said bead of said reaction material to facilitate detection of said analyte. Further, preferably the steps of preloading and the lyophilizing and/or the freeze drying is carried out prior to the step of collecting.

In another aspect, the present teachings provide methods for determining presence and/or a characteristic of a target analyte in a sample. The methods include a step of obtaining a cartridge including multiple reaction wells having contained therein the sample including the target analyte. Then a step of securing includes securing, inside a reaction chamber, the cartridge on a cartridge stage having defined therein an opening such that the cap portion is disposed above the opening and the base portion is disposed below the opening. In this step, the reaction chamber includes a nonlinear-shaped reaction heating block disposed inside a housing disposed below the opening. Further, the reaction heating block has defined therein a heating block aperture that includes an inner heating surface having a curved profile designed to conform to a curved profile of an outer surface of a side portion of the multiple reaction wells. The securing step may further include establishing direct contact of the inner heating surface with the outer surface of the side portion of the multiple reaction wells. The exemplar method for determining presence and/or a characteristic of the target analyte in the sample then proceeds to a step of thermally activating, in the reaction chamber, the analyte using the reaction heating block to render the analyte detectable. By way of example, the step of thermally activating is carried out under isothermal conditions.

The analyte, preferably, includes at least one member selected from a group comprising DNA, RNA, and protein. The step of thermally activating includes amplifying the analyte. The analyte may be a severe acute respiratory syndrome coronavirus 2. The step of thermally activating may include applying one or more different types of energy that is chosen from a group comprising thermal energy, mechanical energy, magnetic energy, electric energy, acoustic energy, radiation energy, and fluidic energy.

The exemplar method for determining presence and/or characteristic of the target analyte in the sample may further include: (i) a step of collecting the sample including the target analyte; (ii) a step of placing the sample in a lysing tube; (iii) a step of introducing the lysing tube in a lysing chamber; (iv) a step of heat treating, using a lysing heating block, the lysing tube to produce a lysed sample; and (v) a step of transferring the lysed sample from the lysing tube to the cartridge. The steps of collecting, placing, introducing, heat treating and transferring are carried out prior to the step of obtaining.

The exemplar method for determining presence and/or characteristic of the target analyte in the sample may further still include a step of preloading the cartridge with at least one reaction material chosen from a group comprising reagent, buffer and probe to form a preloaded cartridge and to facilitate detection of the analyte. In one embodiment of the present teachings, after the step of preloading, a step of lyophilizing and/or freeze drying the reaction materials component may be carried out. In this step, one approach includes lyophilizing and/or freeze drying the reaction materials in each of the multiple reactions wells. In another embodiment of the present teachings, lyophilizing and/or freeze drying the reaction materials is carried out before the step of preloading and outside the multiple reactions wells, to form a bead or a pellet that is subsequently conveyed to each of the multiple reaction wells to form a preloaded cartridge assembly. The steps of preloading and lyophilizing and/or freeze drying are, preferably, carried out prior to the step of collecting.

The exemplar method for determining presence and/or characteristic of the target analyte in the sample may further still include a step of transferring the sample to the cartridge using at least one member chosen from a group comprising syringe, pipette, eye dropper, capillary tube, paper strip, and dipstick.

The methods for determining presence and/or a characteristic of the target analyte in the sample may also involve detecting the analyte. To this end, one such exemplar method may include a step of energizing, using an energy source, non-linearly arranged, multiple excitation light sources to generate multiple incident light beams. Next a step of transmitting includes transmitting, after the step of thermally activating, each of the multiple incident light beams through a corresponding one of the multiple reaction wells to generate multiple emission light beams. Then a step of detecting involves detecting, using multiple photodetectors energized using the energy source, each of the multiple emitted light beams at a corresponding one of the multiple photodetectors. In this step, each of the multiple excitation light sources corresponds to one of the multiple incident light beams, one of the multiple reaction wells, one of the multiple emission light beams, and one of the multiple photodetectors.

The step of detection may be carried out according to many different implementations. In one implementation of the present teachings, the detecting step includes detecting an emission signal generated by a probe. By way of example, the step of detecting an emission signal includes translating the emission signal, using an algorithm, to produce a result that is displayed at a user interface. As another example, the step of detecting the emission signal includes detecting a signature that is at least one member selected from a group comprising optical signature, electrochemical signature, magnetic signature, and mechanical signature.

The step of detecting may include detecting presence of the analyte in a biomolecule sample. In this embodiment, the above-mentioned step of the obtaining includes collecting a sample from of at least one member chosen from a group comprising virus, microbe, bacteria, water, food, beverage, soil, plant, oil, animal tissue, animal byproduct, air, filter of air or water, and item that has contacted food.

In yet another aspect, the present teachings provide methods for collecting target analyte data. One such exemplar method, preferably, begins with energizing, using an energy source, a reaction heating block, a lysing heating block, multiple excitation light sources and multiple photodetectors. Then a step of introducing is carried out and it includes introducing a sample containing a target analyte inside a lysing chamber. Next, a step of lysing includes lysing, using the lysing heating blocked disposed inside the lysing chamber, the sample to produce a lysed sample. The exemplar method then proceeds to a thermally activating step that includes thermally activating, using the reaction heating block disposed inside a reaction chamber, the lysed sample to produce a detectable sample in which the target analyte is rendered detectable. After thermal activation is performed to obtain a detectable sample, a step of detecting is performed. The step of detecting includes detecting, using the multiple excitation light sources and the multiple photodetectors disposed inside the reaction chamber, the detectable sample to determine presence and/or a characteristic of the target analyte in the sample.

The exemplar method may further include a step of transferring the lysed sample to the reaction chamber containing the reaction heating block. The steps of lysing and/or the thermally activating, preferably, include applying one or more different types of energy that is chosen from a group comprising thermal energy, mechanical energy, magnetic energy, electric energy, acoustic energy, radiation energy, and fluidic energy. The step of detecting includes detecting an optical signal generated by a probe and determines an amount of the target analyte present in the sample.

The construction and method of operation of the present arrangement and present teachings, however, together with additional objects and advantages thereof, will be best understood from the following descriptions of specific embodiments when read in connection with the accompanying figures that described below.

BRIEF DESCRIPTIONS OF THE DRAWINGS

DETAILED DESCRIPTION OF THE PREFERRED EMBODIMENTS

In the following description, numerous specific details are set forth in order to provide a thorough understanding of the present arrangements and teachings. It will be apparent, however, to one skilled in the art that the present teachings may be practiced without limitation to some or all of these specific details. In other instances, well-known method steps have not been described in detail in order to not unnecessarily obscure the present arrangements and teachings.

The systems and methods of the present inventions provide a simple, integrated method and a portable, hand-held device for performing an analyte test that determines presence and/or characteristics of one or more target analytes in a sample.

Figure 1:
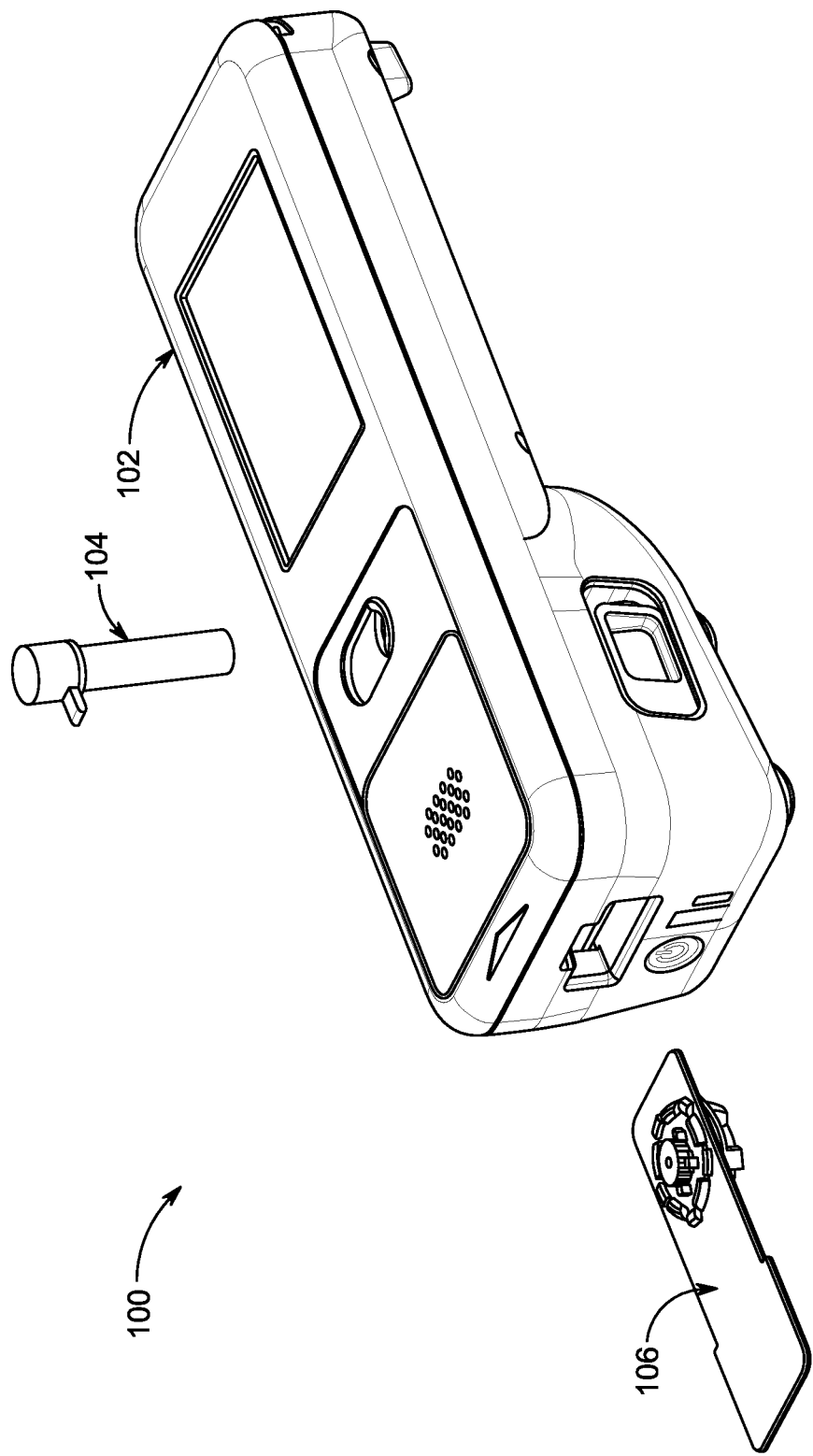
FIG. 1 shows a perspective view of a portable, hand-held target analyte data collecting device, a cartridge card assembly, and a lysing tube, all of which represent one embodiment of the respective arrangements, and that may be used to analyze sample including a target analyte.

FIG. 1 shows a target data analyte detection arrangement 100 for collecting target analyte data, according to one embodiment of the present teachings. Target analyte data collecting arrangement 100 includes a target analyte data collecting device 102, a lysing tube assembly 104 and a cartridge card assembly 106. Target analyte data collecting device 102 has a length that ranges from about 215 mm to about 235 mm, and is, preferably about 226 mm, has a width that ranges from about 80 mm to about 95 mm, and is, preferably about 88 mm, and has a thickness (or height) that ranges from about 50 mm to about 65 mm, and is, preferably, about 57 mm. The weight of target analyte data collecting device 102 ranges from about 1.5 pounds to about 2.5 pounds and is, preferably, about 2 lbs.

As will be explained in connection with FIGS. 3, 4A, and 4B, the lysing tube assembly (substantially similar to lysing tube assembly 104 of FIG. 1) facilitates lysing, in a lysing chamber (explained in FIGS. 4A and 4B), of a sample including a target analyte to produce a lysed sample. Further, in connection with FIGS. 5, 6A-6B, 7A-7B and 8, it is explained that the lysed sample is transferred to the cartridge, or cartridge assembly (substantially similar to cartridge assembly 1031 of FIG. 1), which facilitates thermal activation or thermal processing, in the presence of certain buffer, reagents, and/or probes, the lysed sample (containing the target analyte) to produce a detectable sample. This thermal activation is carried out using a reaction assembly (describe in connection with FIGS. 10A and 10B). An optical detection assembly (described in connection with FIGS. 11A and 11B) detects the target analyte in the detectable sample. In certain embodiments of the preferred arrangements, the same reaction chamber (as explained in connection with FIG. 12) is configured to both thermally activate to produce the detectable sample and detect the target analyte in the detectable sample. Further, the results relating to the target analyzed detection are displayed on a user interface of the device for collecting target analyte data.

Figure 2:
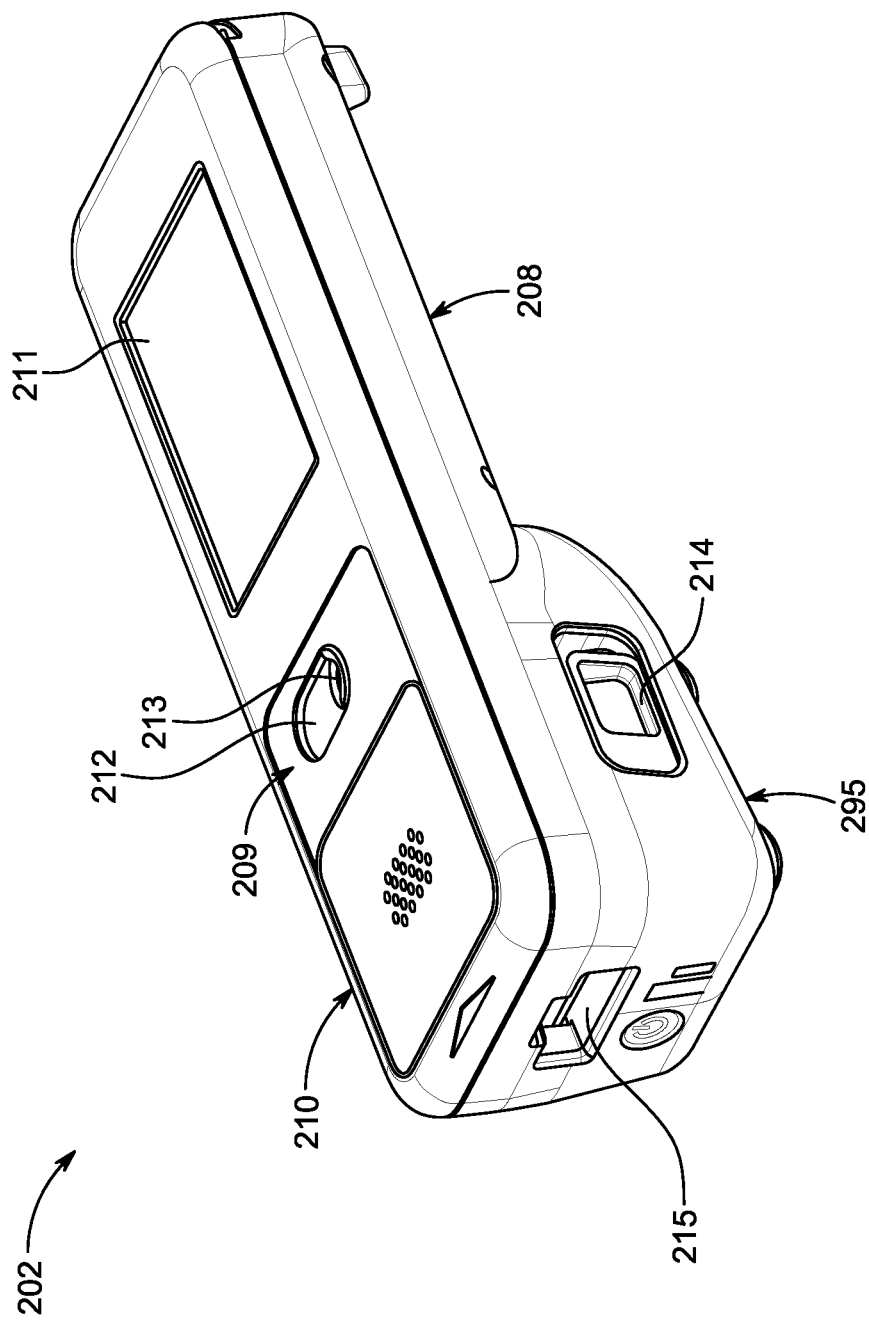
FIG. 2 shows a perspective view of the portable, hand-held target analyte data collecting device of FIG. 1.

FIG. 2 shows a target analyte data collecting device 202, which is substantially similar to target analyte data collecting device 102 of FIG. 1 and includes handle portion 208 and a core assembly portion 295, which, in turn, includes a lysing chamber 209 and a reaction chamber 210. A user interface 211 is provided on a top or loading surface of handle region 208. The top or loading surface at core assembly portion 295 has defined therein a lysing chamber inlet 212 that provides access to a lysing chamber door 213 with a raised lip that is designed to receive a lysing tube (e.g., lysing tube 104 of FIG. 1) when lysing chamber door 213 is open. FIGS. 4A and 4B show additional structural details that may be found inside lysing chamber 209.

In connection with core assembly portion 205, reaction chamber 210 includes a cartridge slot opening switch 214 when placed in an "on" position provides a cartridge card assembly (e.g., cartridge card assembly 106 of FIG. 1) access through cartridge inlet 215 inside reaction chamber 210. According to one embodiment of the present teachings, a sufficient external force, e.g., a user's push, applied to the cartridge secures the cartridge near a cartridge stage (not shown to simplify illustration) inside reaction chamber 210. A cartridge card opening or slot 215, preferably, provides access to optical detection and reaction enabling components disposed inside reaction chamber 210. To this end, FIGS. 10A-10B, 11A-11B, and 12 show such components in detail.

Figure 3:
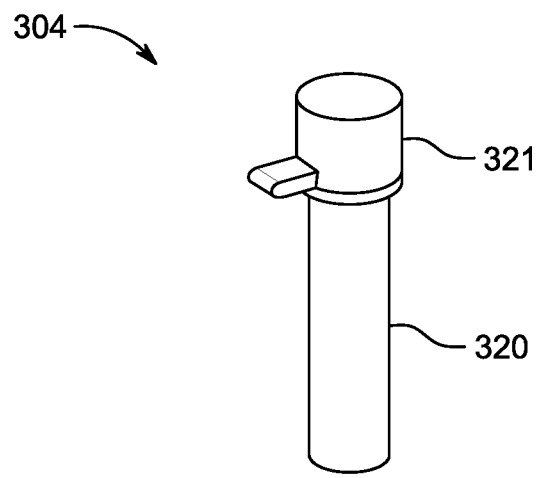
FIG. 3 shows a perspective view of the lysing tube shown in FIG. 1.

Before the cartridge is inserted inside reaction chamber 210, however, contents inside lysing tube assembly 304 of FIG. 3 are transferred to the cartridge. According to this figure, lysing tube assembly 304 has a lysing tube cap 321 and a lysing tube 320. In one embodiment of the present arrangements, lysing tube assembly 304 includes a securing mechanism that secures lysing tube cap 321 to lysing tube 320.

Figure 4A:
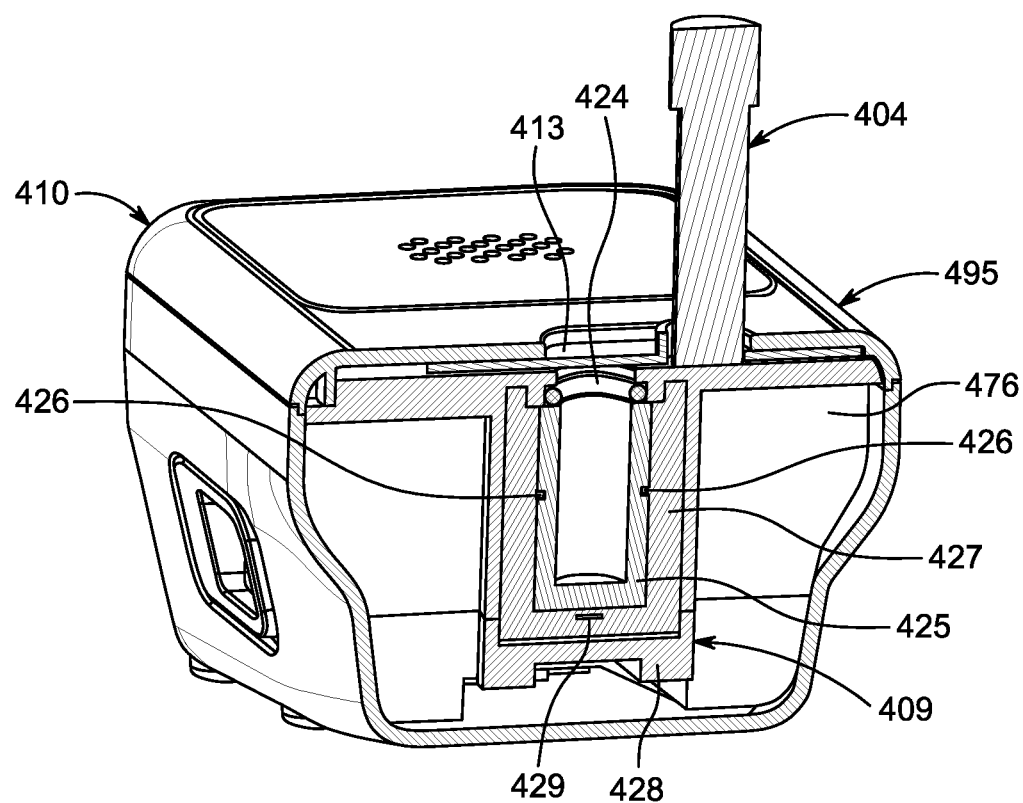
FIG. 4A shows a side-sectional view of the portable, hand-held target analyte data collecting device shown in FIG. 1 and that shows certain salient components/features of a lysing chamber.
Figure 4B:
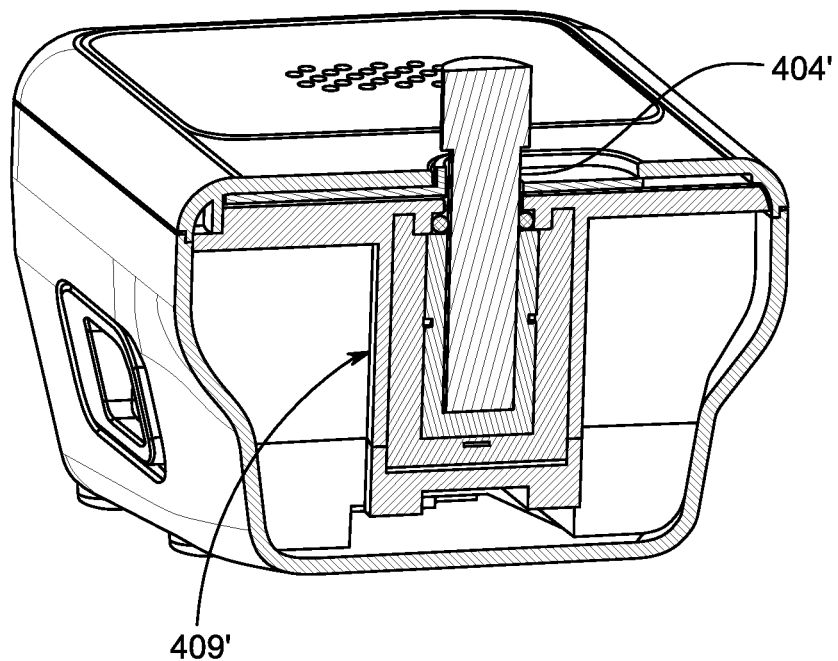
FIG. 4B shows a side-sectional view of the portable, hand-held target analyte data collecting device shown in FIG. 1 having installed therein the lysing tube shown in FIGS. 1 and 3.

A lysing tube 320 loaded with a sample including a target analyte is sealed using lysing tube cap 321 and placed inside lysing chamber 409, which is shown in FIG. 4A. FIG. 4A shows a core assembly portion 495 includes lysing chamber 409 and reaction chamber 410. A separation wall 476 preferably separates lysing chamber 409 and reaction chamber 410.

Lysing chamber 409 includes a lysing chamber housing 428 that preferably houses an insulation 427 for surrounding a heating block 425. A heater input 426, which is disposed adjacent to and is coupled to lysing heating block 425, preferably surrounds heating block 425 to provide thermal energy for application of a thermal regimen. Additional structural details that allow securing lysing tube assembly 404 inside heating block 425 include a lysing chamber door 413 that slides open to provides access to lysing tube assembly 404 and an o-ring that holds in place lysing tube assembly 404 inside heating block 425. FIG. 4B shows a lysing tube assembly 404', which is substantially similar to lysing tube assembly 404, in an inserted state or position inside a heating block of lysing chamber 409.

When lysing tube assembly 404 is secured inside heating block 425, using an energy source (e.g., a battery provided in the target analyte data collecting device), a lysing heating block 425 is energized to lyse the sample contained inside the lysing tube assembly to produce a lysed sample. A temperature sensor 429 is provided to measure temperature at or near heater input 426, which approximates the temperature of the sample inside lysing tube assembly 404. This temperature is conveyed to a printed circuit board that determines the duration of the heat treatment, according to a first thermomechanical regimen, to produce the lysed sample. Application of a thermal regimen to lyse samples in lysing chamber 409 may be automated such that an untrained user may implement the thermal regimen via a user interface.

Lysing tube 420 may be preloaded with a desired buffer and/or reagent prior to placement in lysing chamber 409. In certain embodiments of the present arrangements, such preloaded buffer and/or reagent is lyophilized and/or freeze-dried inside lysing tube 420.

In alternate embodiments of the present arrangements, sample-preparation techniques (i.e., for downstream processing in a reaction chamber) other than lysing are performed in chamber 409. In such manner, lysing chamber 409 may alternatively be considered a sample-preparation chamber. Indeed, the systems of the present arrangement contemplate performing any sample preparation that facilitates extraction of a target analyte from a sample and/or deactivation of one or more compounds in a sample that are inhibitory downstream detection using an assay for a target analyte (e.g., nucleic acid amplification or an enzyme-linked immunosorbent assay indicated by a fluorescent probe).

Figure 5:
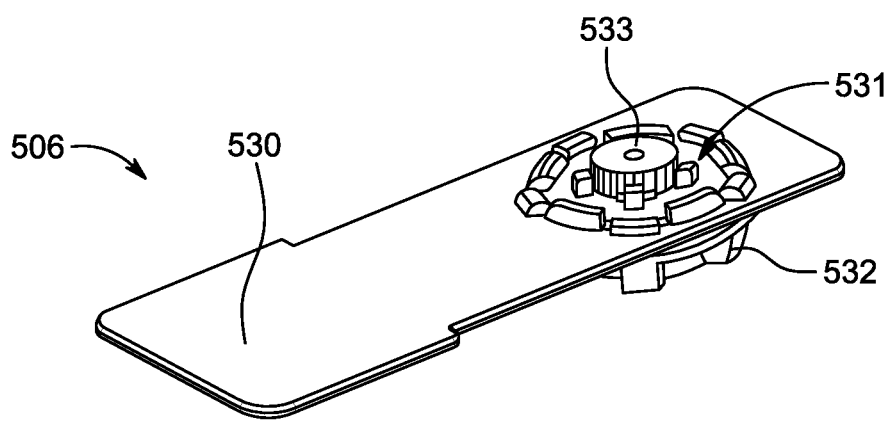
FIG. 5 shows a perspective view of the cartridge card assembly shown in FIG. 1.

FIG. 5 shows a cartridge card assembly 506, according to one preferred embodiment of the present arrangements. Cartridge card assembly 506 is substantially similar to its counterpart described above with reference FIG. 1 (i.e., cartridge card assembly 106 of system 100). Cartridge card assembly 506 includes a rectangular card 530 with a cartridge assembly 531 disposed at or near a first end. Preferably, cartridge assembly 531 is secured within a card opening defined within rectangular card 530. As shown in FIG. 5, rectangular card 530 is configured in a longer, rectangular shape such that a user may handle cartridge card assembly 506 on the end opposite to cartridge assembly 531 (e.g., for insertion into a target analyte data collecting device such as device 102 of FIG. 1). Space on rectangular card 530 may also be used to implement a barcode to track reaction data and results by a target analyte data collecting device configured to implement cartridge card assembly 506, which may also be configured with a barcode reader for such purpose.

Cartridge assembly 531 on cartridge card assembly 506 includes a base portion 532 (described in further detail below with reference to FIGS. 6A-6B) with a cap portion 533 (described in further detail below with reference to FIGS. 7A-7B) secured thereon, preferably by press fitting cap portion 533 onto base portion 532 to engage complementary regions and features. Preferably, base portion 532 is attached to a card opening defined within rectangular card 530. In this preferred embodiment, rectangular card 530 has defined thereon a card opening and includes multiple card attaching features disposed on base portion 532 such that multiple card attaching features connect base portion 532 to said rectangular card 530.

In certain other embodiments of the present arrangements, however, a rectangular card 530 is not used, and cartridge assembly 531, unattached to any card feature, is used to facilitate detection of presence and/or characteristics of a target analyte by systems disclosed herein. The systems and methods disclosed herein contemplate any means of delivering a cartridge for further data collecting and analysis by the target analyte data collecting devices disclosed herein.

Figure 6A:
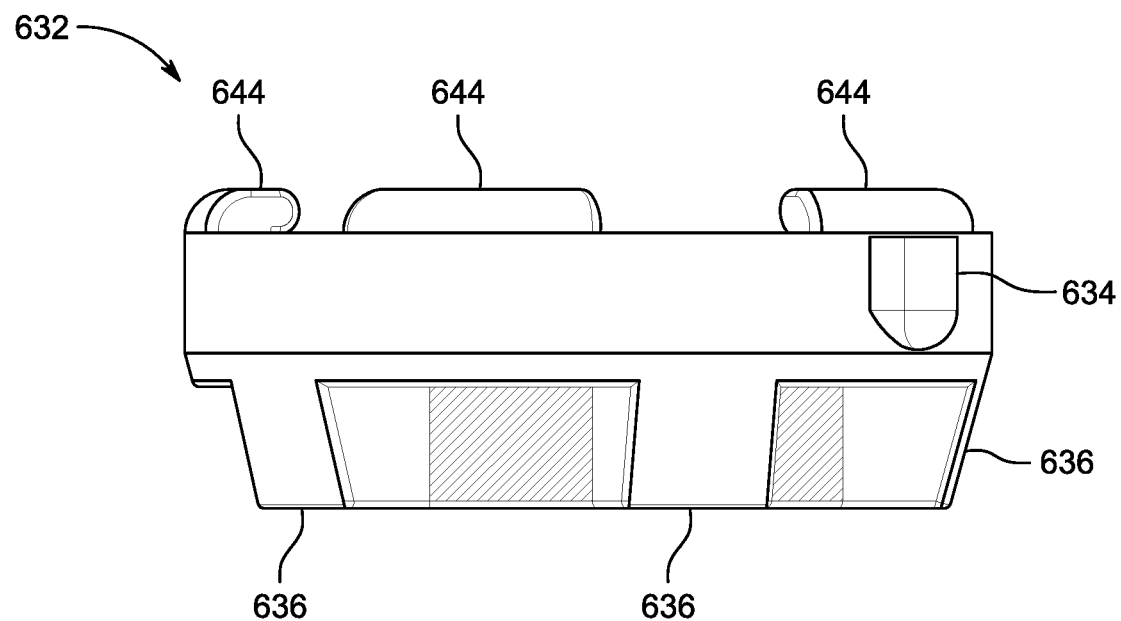
FIG. 6A shows a side view of a base portion, without the cap portion, of the cartridge shown in FIGS. 1 and 5.
Figure 6B:
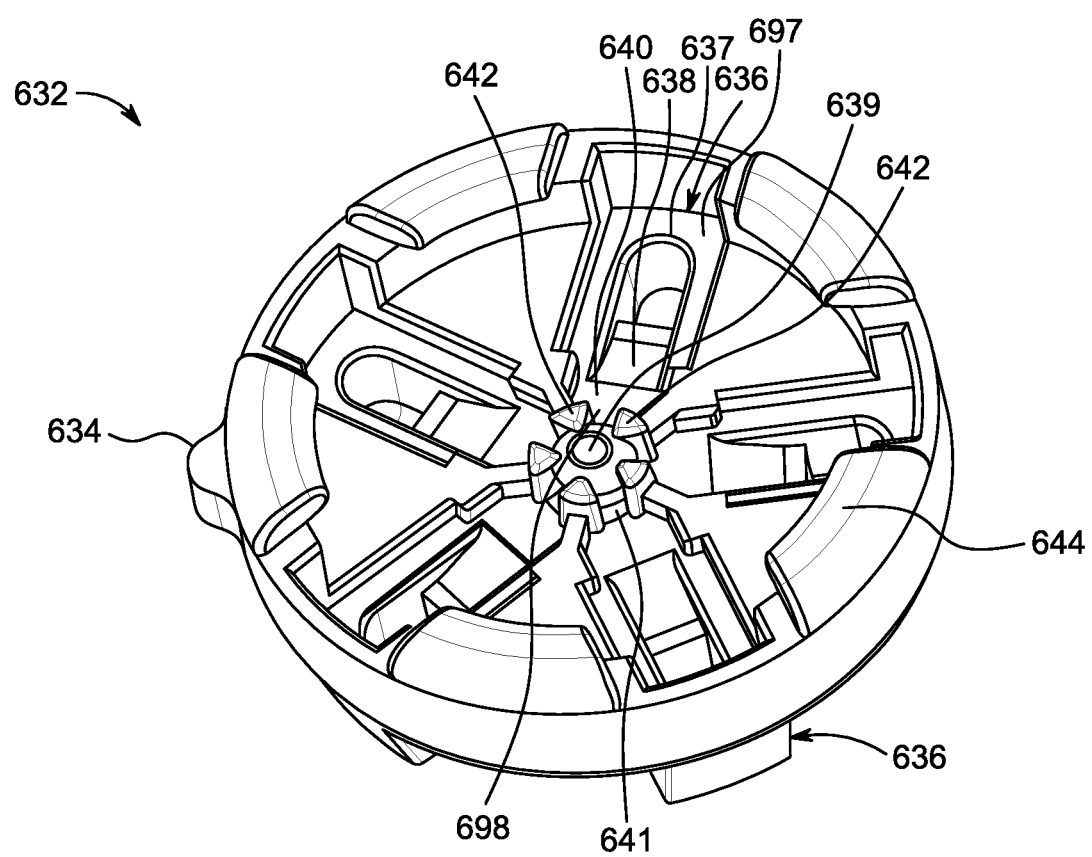
FIG. 6B shows a top perspective view of the base portion shown in FIG. 6A to show salient components/features inside the base portion.

FIGS. 6A and 6B shows features of a base portion 632 that allows the cartridge assembly (e.g., cartridge assembly 531 of FIG. 5) to both serve as a receptacle for reactions and withstand the compression forces that may be encountered during the reactions. Before reaction, and if required, compression, is carried out inside or on the cartridge assembly, a cap portion (e.g., cap portion 533 of FIG. 5) is secured on a base portion (e.g., base portion 532 of FIG. 5) to complete the cartridge assembly (which also may be thought of simply as a "cartridge"). To this end, FIG. 6A shows a base portion 632, which is substantially similar to base portion 532 of FIG. 5, includes multiple securing features 644 that are designed to secure therewithin an edge of the cap portion, such that the cap portion is effectively secured to base portion 632. Further, an orientation key 634 extends from an edge of base portion 632 and away from a center region of base portion 632. In an operative state of the cartridge, orientation key 634 functions in conjunction with an orientation lock disposed on or near cartridge stage (e.g. orientation lock 1073 of FIG. 10A) and is designed to place the cartridge in a desired orientation to allow heating of said sample and/or detection of said target analyte.

To facilitate reactions inside an assembled cartridge, base portion 632 includes multiple reaction well housings 636. The structural details inside each of reaction well housings 636 are shown in FIG. 6B.

According to this figure, base portion 632 includes, at or near a center region, a supporting feature 641 having disposed thereon a receiving area 639 and multiple channel dividers 642 that are radially disposed around receiving area 639. In this configuration, multiple channel entry regions 698 are defined between multiple channel dividers 642 for receiving the sample received at receiving area 639. Multiple connecting tracks 640 substantially linearly extend from receiving area 639 or a region proximate thereto (such as multiple channel entry regions 698) to multiple reaction wells 637. As a result, multiple connecting tracks 640 are designed to convey a sample including said target analyte from receiving area 639 to multiple reaction wells 637. As explained later, each of multiple reaction wells 637 are configured to transform said sample to a detectable sample.

A base portion flow path for the sample is defined from receiving area 639 to each of multiple reaction wells 637 and includes passing through one of multiple channel entry regions 698 and one of multiple connecting tracks 640.

To withstand compression forces, each of connecting tracks 640 includes a second compression resisting region 638 and each of multiple reaction well housings 636 includes a first compression resisting region 697. As shown in FIG. 6B, first compression resisting region 697 and second compression resisting region 638 surround reaction well 637. As will be explained in further detail below with reference to FIG. 8, when cartridge assemblies of the present arrangements are in use, reaction well 637, first compression resisting region 697, and second compression resisting region 638 align with corresponding regions on a cap portion (e.g., cap portion 733, described below with reference to FIGS. 7A-7B) to facilitate sealing of reaction well 637 during reactions, including optical detection reaction.

The open geometry of base portion 632 (i.e., before a cap portion is secured thereon to form a cartridge assembly) provides the advantage of pre-loading reaction materials, such as buffers, reagents and probes for a desired reaction (e.g., an amplification reaction) into each of multiple reaction wells 637. By way of example, a reaction material that includes at least one of buffer, reagent and probe, is pre-loaded into each of multiple reaction wells 637 by removing, using securing features 644, the cap portion and then lyophilizing and/or freeze drying the reaction materials. In this example, a cap portion (e.g. cap portion 732 of FIGS. 7A and 7B) is secured, preferably by press-fitting using securing features 644, onto a preloaded base portion 632 to form a preloaded cartridge assembly, which is readily stored, or transported for later use, for example, in the field. This provides the advantage of such pre-loading steps being performed by trained technicians away from the field such that reactions may be carried out by untrained users in the field. This provides the further advantage of being able to store such reagents, buffers, and/or probes at room temperature, whereas conventional systems may require storage of such reagents, buffers, and/or probes in refrigerators or freezers.

Figure 7A:
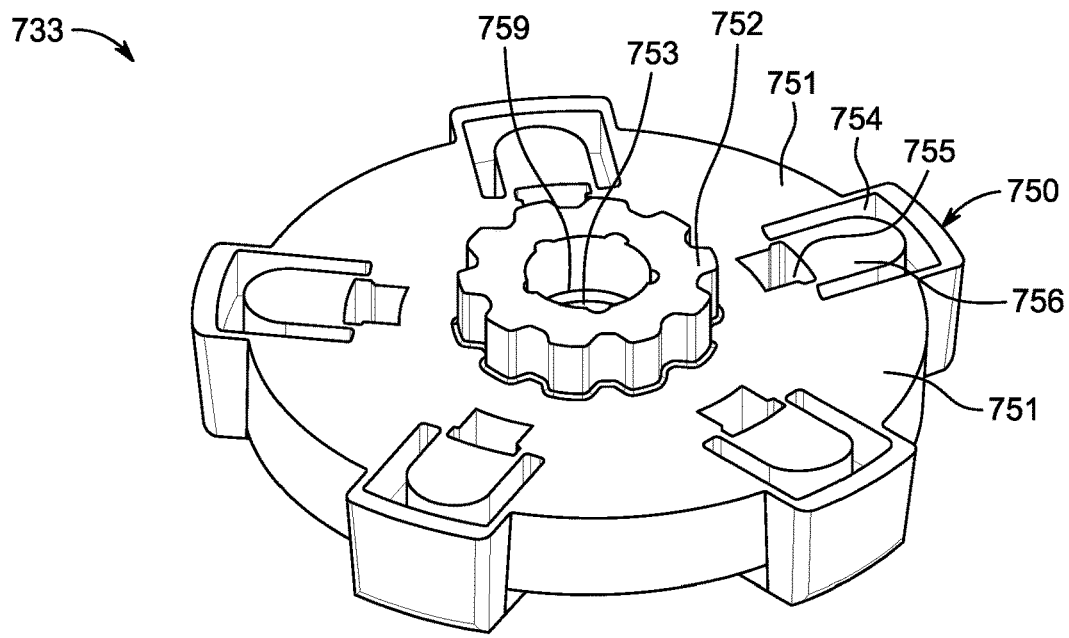
FIG. 7A shows a top perspective view of the cap portion shown in FIG. 7A to show salient components/features inside the cap portion.
Figure 7B:
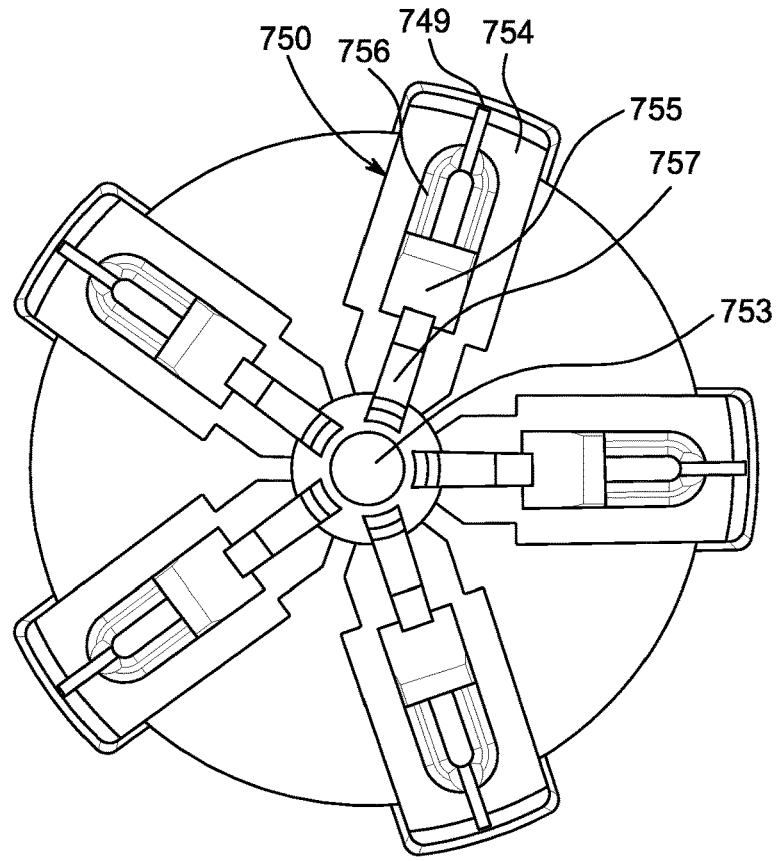
FIG. 7B shows a bottom view of the cap portion of FIG. 7A.

FIGS. 7A and 7B shows a cap portion 733 that includes provisions for effectively carrying both reactions and receiving compression forces. In connection with facilitating reaction, cap portion 733 has defined therein multiple vents 749, which are described in detail in connection with FIG. 8.

Cap portion 733 includes multiple connecting track covers 757 that are disposed adjacent to multiple connecting tracks 640 shown in FIG. 6B. In this configuration, each of multiple connecting track covers 757 cover each of multiple connecting tracks 640 and each of multiple connecting track covers 757 includes a second compression region 755. This portion of second compression region 755 corresponds to or is adjacent to second compression resisting region 638 shown in FIG. 6B in the cartridge assembly.

Multiple reaction well housing covers 750, in complementary fashion, are disposed adjacent to cover multiple reaction well housings 636. Each of multiple reaction well housing covers 750 include a first compression region 754 and second compression region 755 and a reaction well cover 756. In an assembled configuration of the cartridge, multiple first compression regions 754 are adjacent to and combine with multiple first compression resisting regions 697 shown in FIG. 6B, portions of multiple second compression regions 755 are adjacent to and integrate with portions of multiple second compression resisting region 638 shown in FIG. 6B and multiple reaction well covers 756 are adjacent to and combine with multiple reaction wells 637 to effectively seal the bottom portion such that during reaction, vapors of the reactional materials and/or target analyte do not escape.

Figure 8:
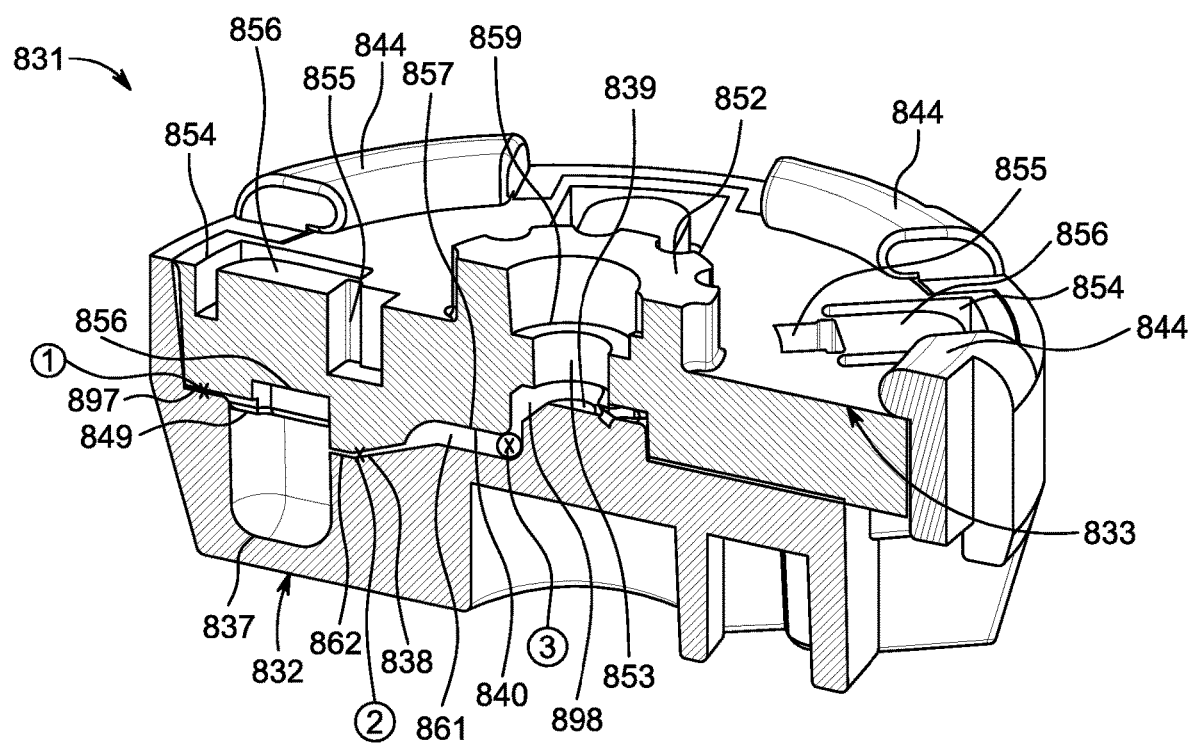
FIG. 8 shows a perspective, side-sectional view of an assembled cap portion and base portion, wherein the cap portion shown in FIG. 7B is secured above the base portion shown in FIG. 6B.

FIG. 8 specifically shows that first compression region 754 and first compression resisting regions 697 combine to form a first seal (i.e. at a location 1 on a cartridge assembly 831) and second compression region 755 and second compression resisting regions 638 combine to form a second seal (i.e., at a location 2 on cartridge assembly 831). Seals at location 1 and location 2 are configured to effectively seal a reaction well during a detection reaction.

According to FIG. 8, cartridge assembly 831 of the present arrangements is substantially similar to it counterpart in FIG. 5 (i.e., cartridge assembly 531). Base portion 832, reaction well 837, first compression resisting region 897, second compression resisting region 838, receiving area 839, channel entry region 898, securing feature 844, and connecting track 840, are substantially similar to their counter parts described above with reference to FIGS. 6A-6B (i.e., base portion 632, reaction well 637, first compression resisting region 697, second compression resisting region 638, receiving area 639, channel entry region 698, securing feature 644, and connecting track 640). Further, cap portion 833, vents 849, gasket 852, inlet port 853, first compressing region 854, second compressing region 855, reaction well cover 856, and third compressing region 859, are substantially similar to their counterparts described above with reference to FIGS. 7A-7C (i.e., cap portion 733, vents 749, gasket 752, inlet port 753, first compressing region 754, second compressing region 755, reaction well cover 756, and third compressing region 759.

Complementary features aligned in cartridge assembly 831 serve multiple purposes in connection with facilitating reactions and undergoing compression, during the reactions. As explained above, seals at locations 1 and 2 in FIG. 8 effectively seal reaction well 837 from receiving additional amounts of sample (including the target analyte) when the sample already present inside reaction well 837 is undergoing a reaction according to a thermomechanical regimen. Specifically, the seal at location 1 will effectively block a respective vent 849, and the seal at location 2 will effectively block a reaction well entrance 862.

In connection with effective flow of sample (including the target analyte) to facilitate a reaction, complementary features on base portion 832 and cap portion 833 align to define a channel 861 that extends from a channel entry region 898 (e.g., defined by channel dividers, such as channel dividers 642 of FIG. 6 B) to reaction well 837 (i.e., through reaction well entrance 862). To this end, as shown in FIG. 8, inlet port 853 aligns with receiving area 839 (i.e., for supply of fluid through channel entry region 898), connecting track 840 (which includes second compression resisting region 838) aligns with connecting track cover 857 (which includes a bottom end of second compression resisting region 855) to define an enclosed channel 861 that has a cross-sectional area.

Enclosed channels 861 include sidewalls that extend from channel entry region 898 to reaction well entrance 862. In certain embodiments of the present arrangements, portions of sidewalls are defined by undercuts in cap portion 833. These portions of the sidewalls may be received into base portion 832 by complementary aligning recesses cut into base portion 832. In other embodiments of the present arrangements, portions of the sidewalls extend from base portion 832, and complementary recesses may be cut into cap portion 833.

Regardless of the manner of forming channels and fabricating sidewalls, sidewalls, if they are used, are preferably raised, from a base of their respective connecting tracks, by a height ranging from about 0.2 mm to about 3.0 mm. Further, in one preferred embodiment, channels 861 of the present arrangements have a cross-sectional area that ranges from about 0.6 mm$^2$ to about 1.0 mm$^2$ and linearly extend by a distance that ranges from about 2 mm to about 12 mm.

FIG. 8 also shows a third compression region 859 disposed on inlet port 853 that may be blocked with compressive force applied to third compression region 859 and/or to gasket 852. Regardless of whether the compression force is applied to third compression region 859 or on or near gasket 852 (which may also be thought of as a third compression region), the compression force in this case serves to block inlet port 853 from ambient conditions. In such embodiments, receiving 839 and/or adjacent features (not shown in FIG. 8 to simplify illustration), which are assembled adjacent to inlet port 853, include a supporting feature (e.g., supporting feature 641 of FIG. 6A) that serves as a third compression resisting region. In these embodiments, where compressive force is applied at or near third compression region 859, a seal at location 3 is created that effective seals off inlet port 853 from ambient conditions. In another embodiment, one dimension of said inlet port ranges from about 1 mm to about 5 mm and to the extent inlet port 853 is circular in shape, it has an inlet port diameter that ranges from about 3.5 mm to about 3.8 mm.

In a non-compressed state of cartridge assembly 831, vents 897 may be considered "open" such that they are configured to regulate fluid flow through channel 861 and provide for relatively equal distribution of sample (including the target analyte) and/or mixture (e.g., lysate) in reaction wells 837.

First, open vents 897 provide and escape path for air that is being displaced by fluid and/or mixture during filling of reaction wells 837. Second, vents 897 are configured at a cross-sectional area that is large enough to accommodate air flow but small enough to effectively restrict fluid flow therethrough. Accordingly, a vent 749 may configured at a height in well 837 such that when fluid reaches vent 849, resistive forces caused by the fluid covering vents 849 prevent or substantially reduce filling of fluid in that reaction well. Thus, if one reaction well fills faster, resistance created by contact of the fluid with vent 849 will prevent or substantially inhibit further fluid flow into that reaction well, filling of other reaction wells will continue until similar resistive forces caused by blocking of vents 849 restrict fluid flow into those reaction wells. According to preferred embodiments of the present arrangements, vents 849 are configured to provide a relatively even distribution of fluid or mixture (e.g., lysate) that is delivered through inlet port 853.

In other words, a vent 849 is configured to have a cross-sectional area that facilitates air flow, but significantly inhibits or blocks fluid flow. Preferably, vent 849 has a cross-sectional area that is a value that is between about 0.01 mm$^2$ and about 0.25 mm$^2$ to accomplish this. Further, as shown in FIG. 7B, vents may incorporate various angles (e.g., a t-shaped configuration) to use angles to further implement resistive force preventing fluid flow therethrough.

According to one embodiment of the present arrangements, each of reaction wells 837 has a volume that ranges from about 5 microliters to about 100 microliters and has a diameter that ranges from about 1 mm to about 4 mm. Although FIGS. 6A, 6B and 8 show arranged in a circular configuration on a generally circular base portion 832, the present teachings are not so limited and reactions wells 837 may be arranged in a non-linear configuration on a base portion that is of a non-linear shape.

According to one embodiment of the present arrangements, cap portion 833 is comprised of optically transparent material (which allows for interrogation of optical signals from within a reaction chamber). By way of example, cap portion 833 is comprised of at least one member chosen from a group comprising silicone rubber, polydimethylsiloxane, and a thermoplastic elastomer. Preferably, cap portion 833 comprises a relatively flexible, elastomeric material.

According to another embodiment of the present arrangements, base portion 832 is comprised of material that is optically transparent (which allows for interrogation of optical signals from within a reaction chamber), as well as relatively rigid, such that base portion 832 can maintain high dimensional tolerance (i.e., during compression). According to one embodiments of the present arrangements, base portion 832 is comprised of polypropylene or cyclic olefin copolymer. Use of such materials not only facilitates press fitting of cap portion 833, which is preferably relatively flexible, into base portion 832, which is relatively rigid, but also allows for compression, if required during the reactions that render the sample including the target analyte detectable.

Figure 9A:
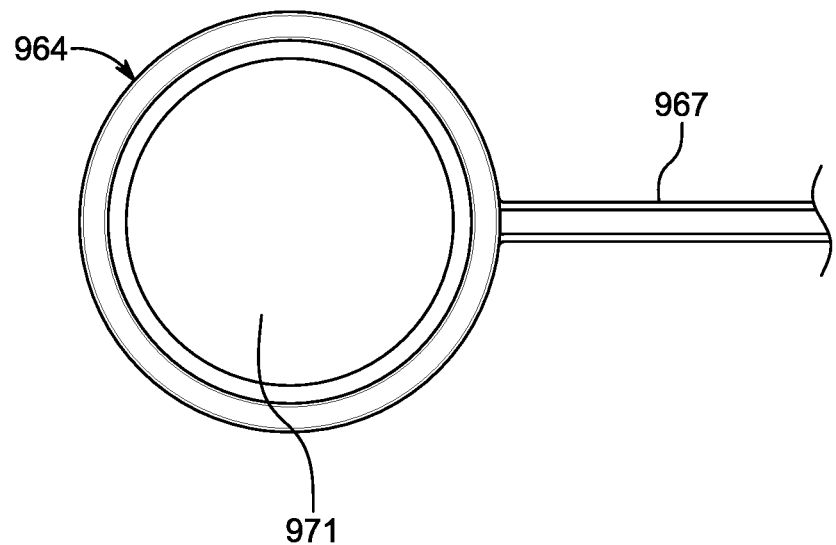
FIG. 9A shows a top view of a non-linear shaped reaction chamber heating block, according to one embodiment of the present arrangements.

FIG. 9A shows a reaction heating block 964, according to one embodiment of the present arrangements. Reaction heating block 964 has defined therein a heating block aperture 971.

As shown in FIG. 9A, reaction heating block 964 has a circular shape with a corresponding circular heating block aperture 971 defined therein. Preferably, heating block aperture 971 is configured to secure a cartridge assembly (e.g., cartridge assembly 831 of FIG. 8). Reaction chamber heating block and/or heating block aperture 971 may be of a non-linear shape.

A heating element 967 is shown connected to an outer surface of reaction heating block 964. A temperature sensor may also be coupled to reaction heating block 964. Preferably, a script running on a computer element (e.g., a printed circuit board) is communicatively coupled to the temperature sensor and heating element 967 in a closed-feedback loop to control temperature conditions during thermally activating steps (including isothermal heat treatment) carried out inside the reaction chambers of the present arrangements. Such precise control of reaction chamber temperatures, including maintaining isothermal conditions, may be facilitated by use of one or more components that facilitate temperature control (e.g., a heating element, a thermistor, and/or a temperature sensor).

Figure 9B:
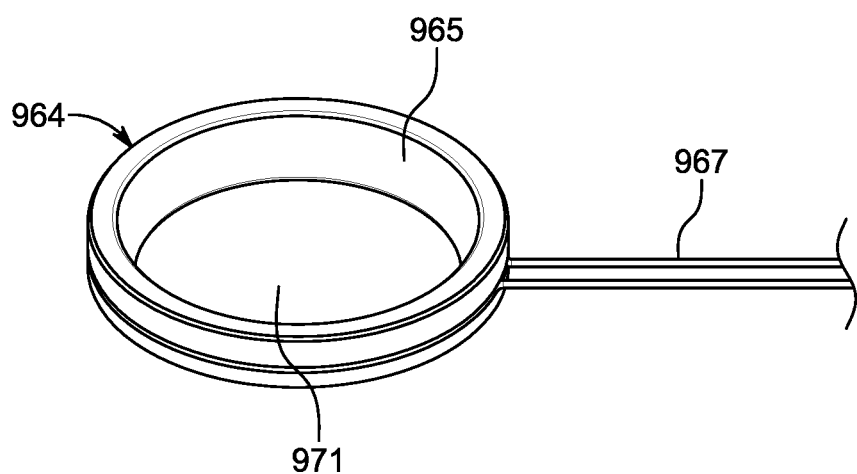
FIG. 9B shows a side-sectional view of the heating block shown in FIG. 9A.

FIG. 9B shows the same reaction hearting block as shown in FIG. 9A, except the FIG. 9B clearly shows features and/or components that are clearly visible from a side view. By way of example, FIG. 9B shows an inner heating surface 965. Inner heating surface 965 may be thought of as a surface that heats a portion of the outer surface of each of the multiple reaction wells (e.g., reaction wells 837 of FIG. 8) during the reaction carried out in the reaction chamber of the present arrangements.

Preferably, inner heating surface 965 has a curved profile that conforms to a curved profile of an outer surface of a side portion of multiple reaction wells. As a result, upon direct contact of inner heating surface 965 with the outer surface of the side portion of the multiple reaction wells, reaction heating block 964 effectively thermally activates samples including target analyte contained inside one or more reaction wells. Stated another way, during an operative state of reaction heating block 964, a cartridge is secured within heating block aperture 971 such that a curved profile of inner heating surface 965 conforms to a curved profile of an outer surface of a side portion of multiple reaction wells to effectively thermally activate multiple samples including target analyte contained inside reaction wells. In other embodiments of the present arrangements, however, the inner heating surface 965 need not necessarily conform to a curved profile of an outer surface of a side portion of multiple reaction wells. Further, the outer surface of reaction wells, which contacts the inner heating surface, need not necessarily have a curved profile.

Preferably, reaction heating block 964 has a diameter that ranges from about 10 mm to about 50 mm, a diameter of heating block aperture 971 ranges from about 3 mm to about 48 mm, and a height of reaction heating block 964 has a value that ranges from about 1 mm to about 20 mm.

In preferred embodiments of the present arrangements, inner heating surface 965 of reaction heating block 964 is configured to slope or taper slight inward to facilitate securing of a corresponding cartridge assembly therein. According to such embodiments, an inner diameter (i.e., diameter of aperture 971) at a top end of reaction heating block 964 is preferably about 5%-15% larger than an inner diameter at a bottom end of reaction heating block 964. According to one preferred embodiment of the present arrangements, reaction heating block 964 has an inner diameter of between about 23 mm to about 29 mm at a top end, and an inner diameter of about between 20 mm to about 25 mm at a bottom end.

Though not shown in FIGS. 9A and 9B, heating block 964 may be secured within a reaction chamber by one or more alignment ribs disposed inside a housing. According to one embodiment of the present arrangements, one or more alignment ribs are disposed around reaction heating block 964 and effectively contact an outer heating surface of reaction heating block 964 to secure and prevent its displacement during thermal processing of samples containing target analytes. The present teachings recognize, however, contact of such alignment ribs with heating block 964 may act as "heat sinks" that draw heat away from reaction heating block 964 during thermal processing of samples containing target analytes. To this end, the present teachings recognize that the number of such contact points and the surface area of contact between heating block 964 and support elements should be minimized. Preferably, alignment ribs, as well as certain other components disposed near reaction heating block 964 or a lysing heating block (e.g., lysing heating block 425 of FIG. 4A) are comprised of insulative, temperature resistance material such as polyether ether ketone, polyoxymethylene, polyphenylene sulfide, polysulfone, polyethersulfone, and/or nylon.

Figure 10A:
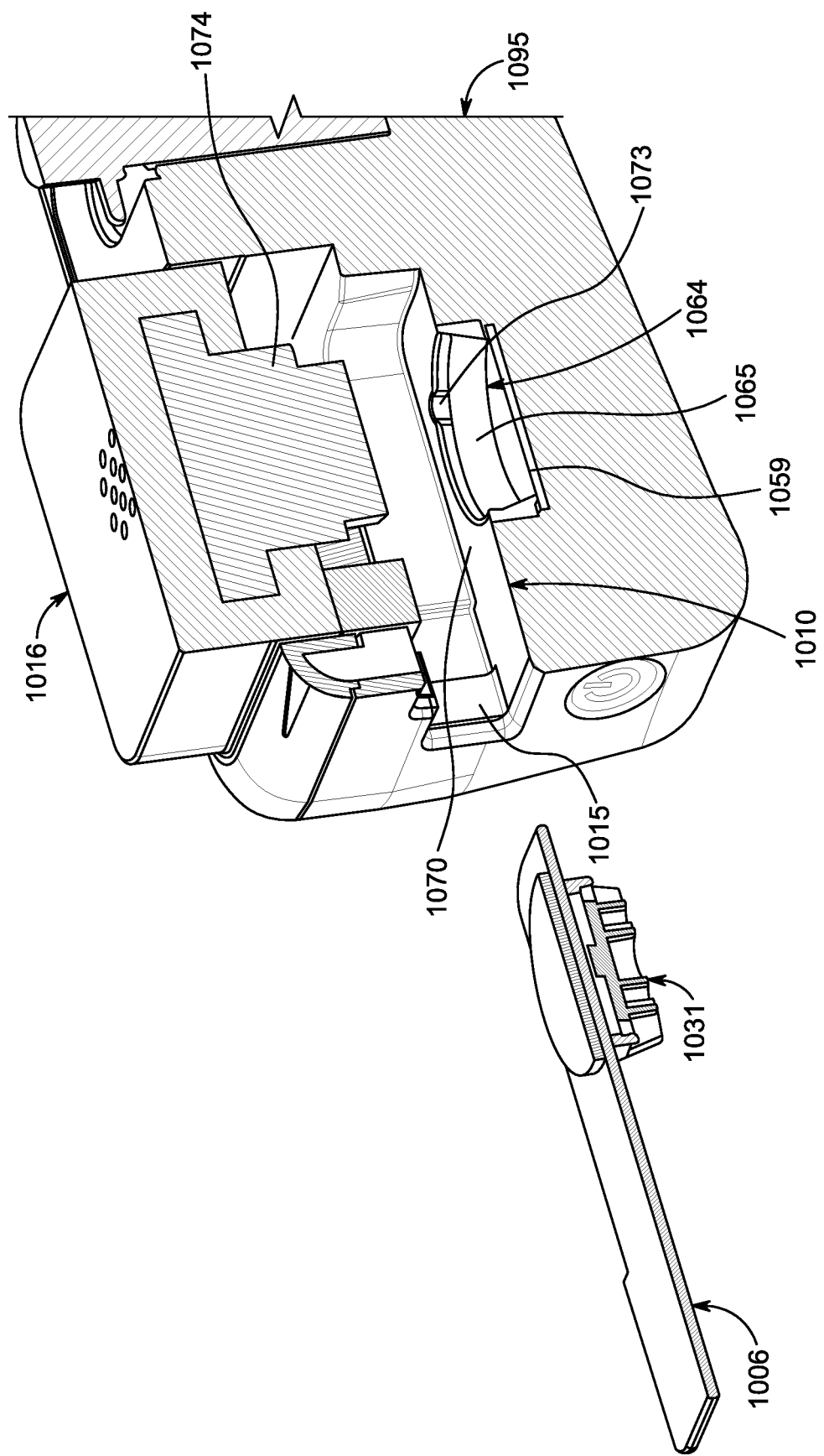
FIG. 10A shows a perspective, side-sectional view of the cartridge card assembly shown in FIG. 1 and of the core assembly portion, according to one embodiment of the present arrangements and that is a part of the portable, hand-held target analyte data collecting device of FIG. 1.

FIG. 10A shows a cartridge card assembly 1006 prior to its insertion into a reaction chamber 1010, according to one embodiment of the present arrangements. Cartridge card assembly 1006 is substantially similar to its counterpart in FIG. 1 (i.e., cartridge card assembly 106) and includes a cartridge assembly 1031 (which is substantially similar to its counterpart in FIG. 8, i.e., cartridge card assembly 831) secured therein.

Reaction chamber 1010 includes a cartridge card assembly opening or slot 1015 substantially similar to cartridge card assembly opening 215 of FIG. 2 and includes a retractable cartridge door 1016 that expands and retracts to provide access to an assembly of optical elements disposed inside reaction chamber 1010. A compression module 1074, in accordance with one embodiment of the present arrangements, is shown connected at a bottom end of cartridge door 1016. Reaction chamber 1010 also includes a reaction heating block 1064 with an inner heating surface 1065, which are substantially similar to their counterparts in FIG. 9A (i.e., reaction heating block 1064 and inner heating surface 965). FIG. 10A also shows a cartridge support film 1059 secured at a bottom end of reaction heating block 1064 and an orientation lock 1073 disposed at a top end of reaction heating block 1064. Reaction heating block 1064 is shown disposed adjacent to a cartridge stage 1070.

In FIG. 10A, reaction chamber 1010 is shown in an open state, exposing salient features and/or components. In this figure, cartridge door 1016 is in a raised position such that cartridge card opening 1015 is open and capable and receiving cartridge card assembly 1006 for placement in reaction heating block 1064.

Figure 10B:
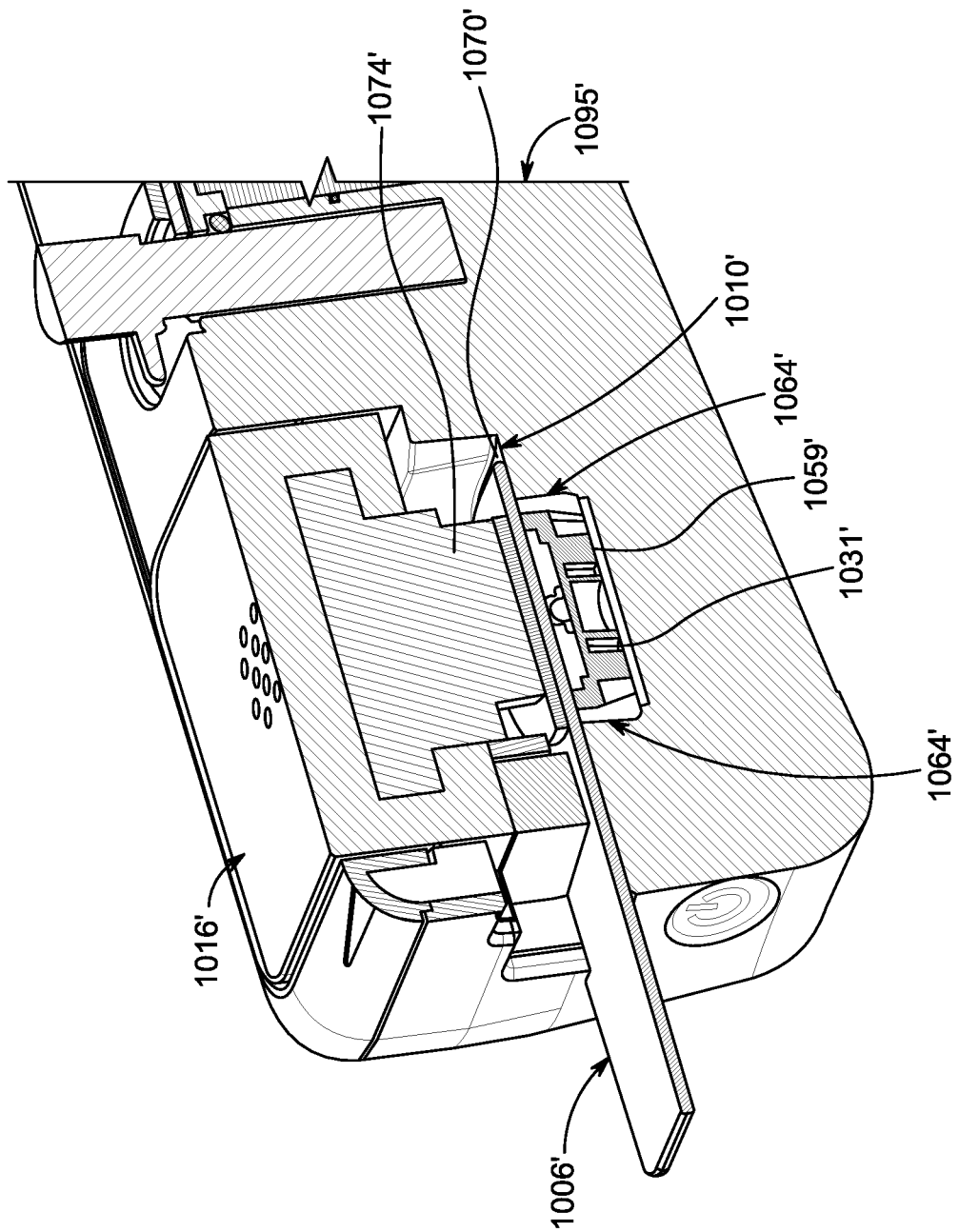
FIG. 10B shows a perspective, side-sectional view of the cartridge card assembly disposed inside the core assembly portion shown in FIG. 10A.

FIG. 10B shows a reaction chamber 1010', according to one embodiment of the present arrangements, with a cartridge card assembly 1006' inserted therein. A cartridge card assembly 1006', a cartridge assembly 1031', a reaction chamber 1010', a cartridge card assembly opening 1015', retractable optical detection assembly components 1016', a compression module 1074', a reaction heating block 1064', a cartridge support film 1059', an orientation lock 1073', and a cartridge stage 1070, are substantially similar to their counterparts in FIG. 10A (i.e., cartridge card assembly 1006, a cartridge assembly 1031, reaction chamber 1010, cartridge card assembly opening 1015, retractable optical detection assembly components 1016, compression module 1074, reaction heating block 1064, cartridge support film 1059, orientation lock 1073, and cartridge stage 1070).

FIG. 10B shows a cartridge card opening 1015 in a closed position with cartridge assembly 1031' secured on a cartridge stage opening such that the base portion is contacting reaction heating block 1064'. FIG. 10B may be thought of as depicting the state of reaction chamber 1010' during thermal processing of samples containing target analyte (e.g., lysate) in cartridge 1031'.

Cartridge support film 1059' disposed adjacent to the reaction heating block is designed to mechanically support cartridge 1031 under compression. To facilitate compression, reaction chamber 1010' may include a compression module such as compression module 1074' of FIG. 10B that, during an operative state of the reaction chamber, compresses a cap portion of cartridge assembly 1031' against a complementary base portion, which contacts inner heating surface of reaction heating block 1064'. The cap portion when secured to a base portion is configured to prevent escape of vapor from the multiple reaction wells and/or to prevent cross-contamination between the different multiple reaction wells. Moreover, placing the cap portion under compressive force further facilitates preventing escape of vapor and cross-contamination between the different reaction wells.

Figure 11A:
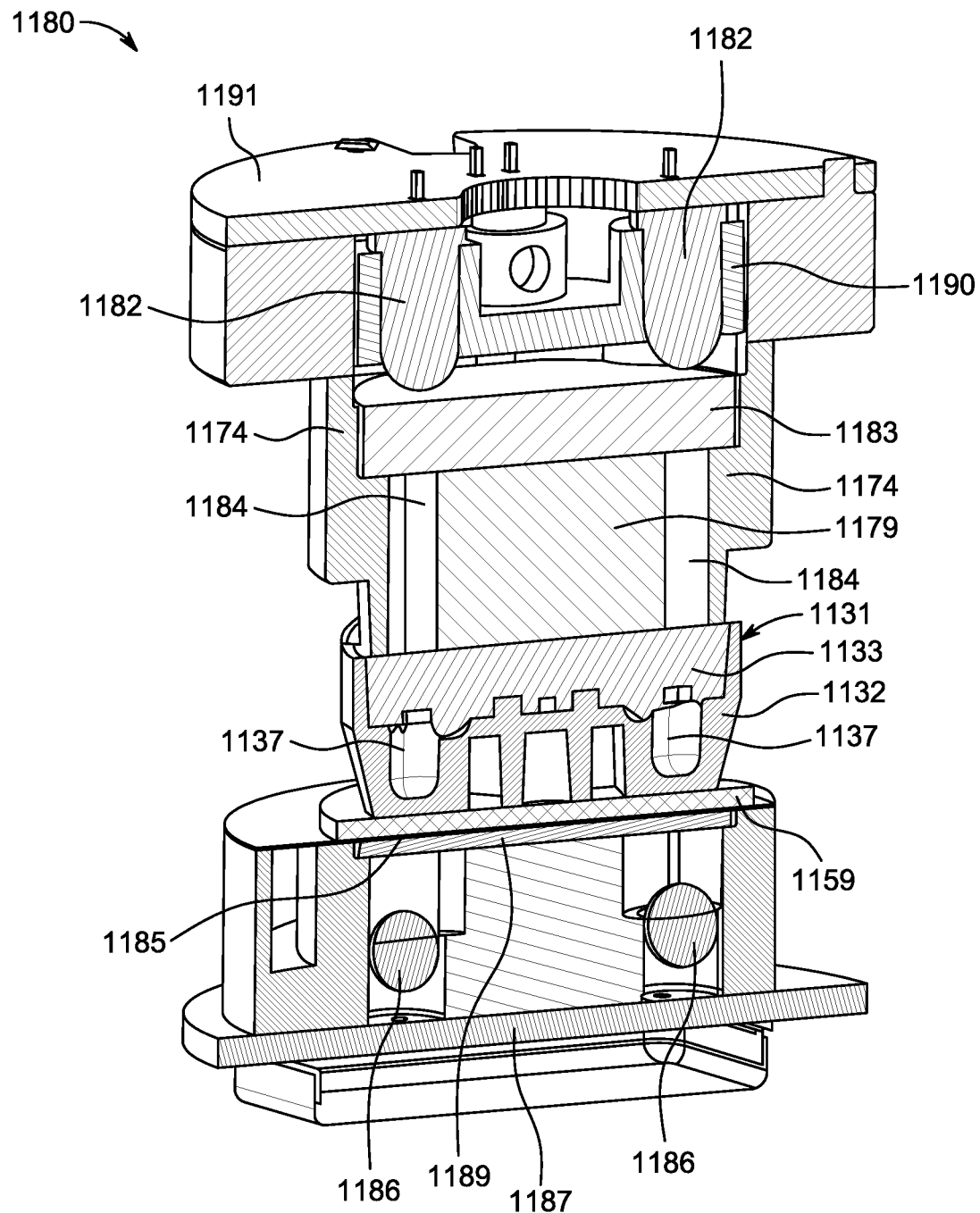
FIG. 11A shows a side-sectional view of the salient components/features of an optical detection assembly, according to one embodiment of the present arrangements and that is part of the core assembly portion shown in FIG. 10A.

FIG. 11A shows an optical detection assembly 1180 with a cartridge assembly 1131 secured therein, according to one embodiment of the present arrangements. FIG. 11A includes a printed circuit board 1191, an excitation light source 1182, an alignment key 1190, an excitation filter 1183, a compression module 1174 with light channels 1181 disposed therein, detection wells 1137, a cartridge support film 1159, an aperture cover 1185, an emission filter 1189, photodetectors 1186, and a photodetector plate 1187. Cartridge assembly 1131 includes a cap portion 1133 and a base portion 1132 having reaction wells 1137 disposed therein.

As shown in FIG. 11A, cartridge assembly 1131 may be thought of as being in a compressed state such that compression module 1174 delivers compressive force to cap portion 1133 and that force is also received by base portion 1132.

Printed circuit board 1191 is a uniquely placed printed circuit board capable of driving the optical detection methods described herein.

Excitation light source 1182 is an excitation light source that produces light at a peak intensity centered at an excitation wavelength of any probe (e.g., fluorophore) used to detect presence and/or characteristics one or more target analytes in a reaction well. Preferably, a peak intensity of excitation light source 1183 is adjusted based on choice of probe and/or fluorophore used for optical detection of analytes and analyte characteristics in reaction wells. According to one embodiment of the present arrangement, a peak intensity of excitation light source 1182 is centered at a wavelengths of about 480 nm.

According to one embodiment of the present arrangements, an excitation light source is at least one member chosen from a group comprising light emitting diode, laser, and gas lamp.

Alignment key 1190 is a structural element configured to receive and to facilitate alignment of excitation light source 1183 with other features of optical detection assembly 1180 and/or a reaction well that are disposed within optical detection assembly 1180 (e.g., reaction well 1137).

Alignment key 1190 is preferably comprised of an opaque polymer that is not auto-fluorescent or excitable by light delivered by photodetectors 1182 during optical detection.

Excitation filter 1183 preferably blocks all wavelengths from excitation light source 1182 that would overlap from an emission signal from a probe and/or fluorophore. According to one embodiment of the present arrangements, excitation filter 1183 is a short pass filter that blocks all wavelengths above about 500 nm.

Compression module 1174 is a component used to compress cartridge assembly 1131 and seal reaction wells 1137 during the reactions of the present teachings that are susceptible to optical detection. According to the embodiment of FIG. 11A, compression module 1174 also includes one or more light channels 1184 disposed therein to facilitate transfer of light that passes through excitation filter to reach reaction wells 1137. Preferably, light channels 1184 are longitudinally aligned with excitation light sources 1182.

As shown in FIG. 11A, a cartridge assembly 1131 having a base portion 1132 with a cap portion 1132 secured thereon is shown disposed under light channels 1184. Preferably, light channels 1184 are longitudinally aligned with reaction wells 1137 disposed inside cartridge assembly 1131.

As shown in FIG. 11A, compression module 1174 presses against and into cartridge assembly 1131. To this end, cartridge assembly 1131 may be thought as being in a compressed state.

As shown in FIG. 11A, cartridge assembly 1131 is shown supported by cartridge support film 1159, which is disposed on aperture cover 1185. Cartridge support film 1159 and/or aperture cover 1185 provide mechanical stability for cartridge assembly 1131 when maintained in a compressed state during the optical detection reactions of the present invention. Aperture cover 1185 may have defined therein small apertures that longitudinally align with the bottom of each of reaction wells 1137. These small holes are configured to prevent crosstalk between light that passes through each of reaction wells 1137.

Cartridge support film 1159 (which is substantially similar to its counterpart in FIG. 10A, i.e., cartridge support film 1059), is comprised of optically transparent material that does not absorb light in the range of common organic fluorescent dyes associated with probes and/or fluorophores for optical detection. Preferably, cartridge support film 1159 is of sufficient rigidity to support cartridge 1131 during compression. According to one embodiments of the present arrangements, cartridge support film 1159 is comprised of cyclic olefin polymer.

Aperture cover 1185 is preferably comprised of material that is opaque, even when in the form of a film or thin sheet, such as stainless steel.

The present teachings recognize that when filtered excitation light (e.g., incident light generated by excitation light source 1182 that has been filtered by excitation filter 1183) reaches a probe and/or fluorophore in a reaction well, the probe and/or fluorophore is excited such that, as a response, it will emit light at a relatively higher wavelength (i.e., a wavelength that is similar to or greater than wavelengths that were blocked by excitation filter 1183). To this end, optical detection assembly 1180 implements emission filter 1189 beneath aperture cover 1185 to allow passthrough of light wavelengths emitted by a probe and/or fluorophore and to filter out excitation wavelengths from advancing. Light that passes through emission filter 1189 may be thought of as an emission signal. In one preferred embodiment of the present arrangements, emission filter is a 510 nm long pass filter.

Excitation filter 1183 and/or emission filter 1187 are preferably comprised of a glass or polymer substrate having a coating or dye that provides sufficient pass-through properties to facilitate detection of presence or characteristics of one or more target analytes.

Photodetectors 1186 are configured to receive an emission signal that propagates from emission filter 1189 and to convert the emission signal (i.e., an optical signal) to an electrical signal that is coupled to various computer elements (e.g. a printed circuit board) for further processing and interpretation of optical detection reactions carried out in reaction wells 1137, including detection of one or more target analytes. Preferably, photodetectors 1186 are longitudinally aligned with reaction wells 1137. Photodetectors 1186 may be at least one member chosen from a group comprising photodiode, photoresistor, and CMOS sensor.

Photodetector plate 1187 rests beneath and/or supports photodetectors 1186. Photodetector plate 1187 is preferably configured to longitudinally align photodetectors 1186 with reaction wells 1187 and/or to prevent cross-talk of emission signals.

Figure 11B:
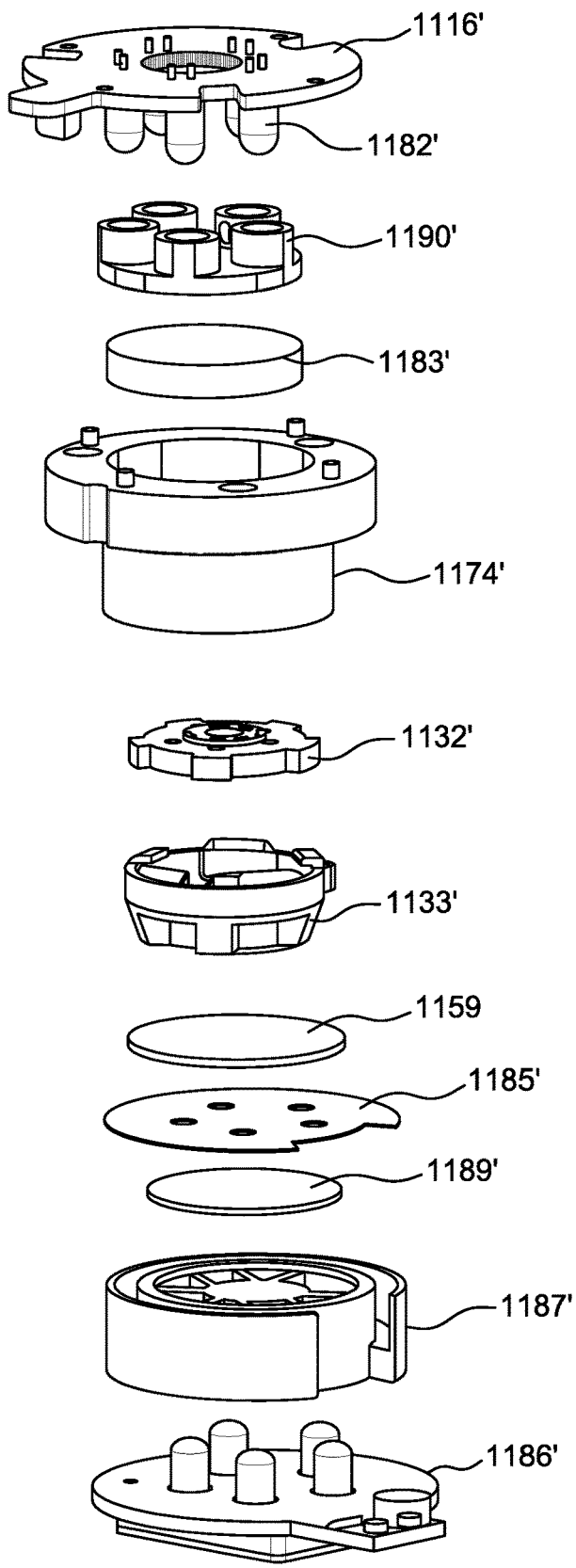
FIG. 11B shows an exploded view of the salient components/features of the optical detection assembly shown in FIG. 11A.

FIG. 11B shows an exploded view of the components shown in FIG. 11A. An optical detection assembly 1180', a printed circuit board 1191', an excitation light source 1182', an alignment key 1190', an excitation filter 1183', a compression module 1174' with light channels 1181' disposed therein, a cartridge cap portion 1133', a cartridge base portion 1132', detection wells 1137', a cartridge support film 1159', an aperture cover 1185', an emission filter 1189', photodetectors 1186', and a photodetector plate 1187', are substantially similar to their counterparts in FIG. 11A (i.e., optical detection assembly 1180, printed circuit board 1191, an excitation light source 1182, alignment key 1190, excitation filter 1183, compression module 1174 with light channels 1181 disposed therein, cartridge cap portion 1133, cartridge base portion 1132, detection wells 1137, cartridge support film 1159, aperture cover 1185, emission filter 1189, photodetectors 1186, and photodetector plate 1187).

Figure 12:
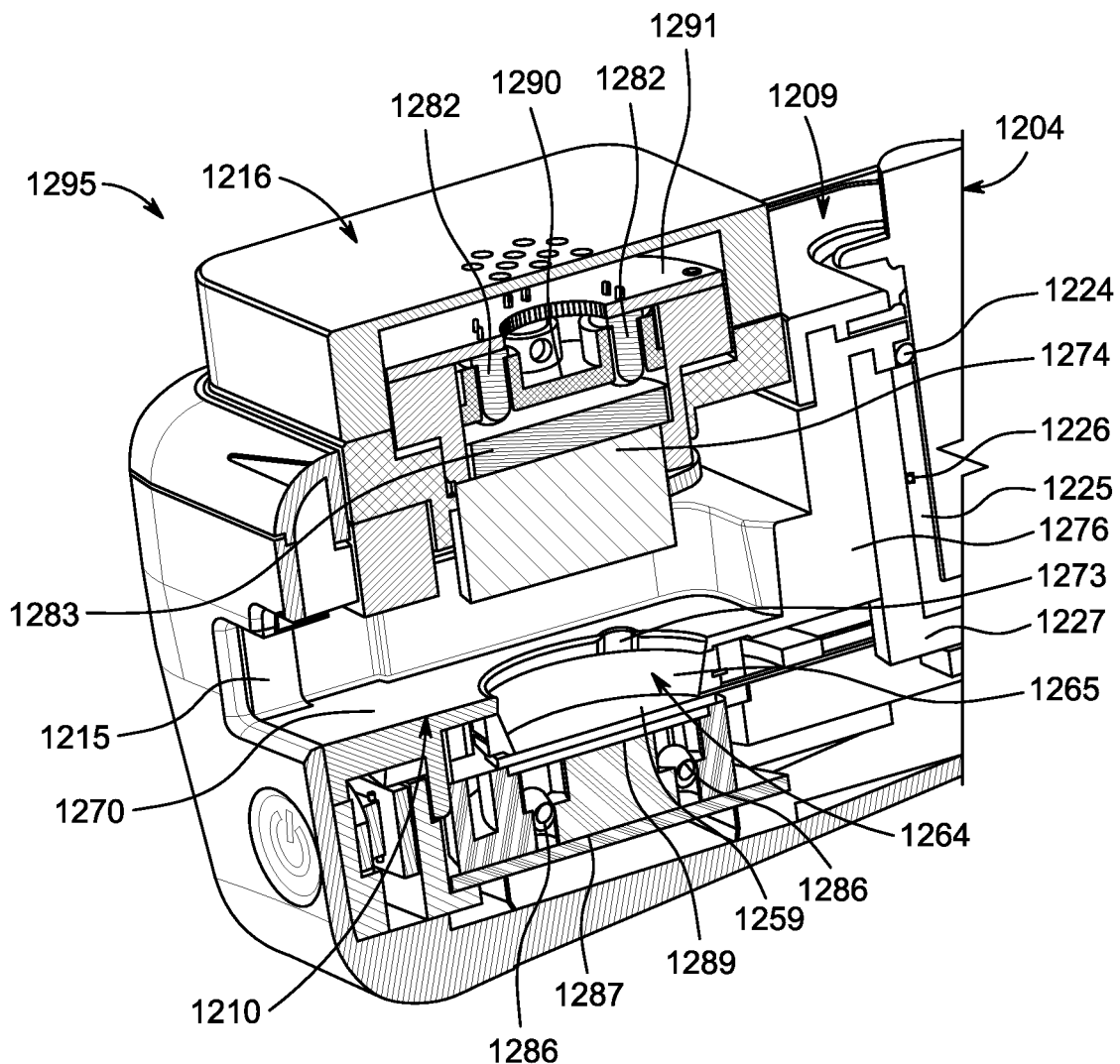
FIG. 12 shows a side-sectional view of the integration of the salient components/features of the optical detection assembly of FIG. 11A and of the reaction assembly that are both part of the core assembly portion shown in FIG. 10A.

FIG. 12 shows certain components of a core assembly portion 1295 of an exemplar target analyte data collecting device, according to one embodiment of the present arrangements. FIG. 12 includes a lysing chamber region 1209 with lysing tube assembly 1204 disposed therein, an o-ring 1224, a lysing heating block 1225, a heating element 1226, and an insulation 1227, which are substantially similar to their counterparts in FIG. 4A, i.e., lysing chamber region 409, lysing tube assembly 404, o-ring 424, lysing heating block 425, heating element 426, and insulation 427. FIG. 12 also shows a separation 1276 separating lysing chamber region 1209 from a reaction chamber region 1210. Reaction chamber region 1210 includes a cartridge card opening 1215, a cartridge state 1270, a reaction heating block 1264, with an inner heating surface 1265 disposed therein, a cartridge stage 1270, an orientation lock 1273, and a cartridge support film 1159, which are substantially similar to their counterparts in FIG. 10A, i.e., separation 1076, reaction chamber region 1010, cartridge card opening 1015, cartridge stage 1070, reaction heating block 1264, and inner heating surface 1065). FIG. 12 also shows certain optical detection assembly components integrated with reaction chamber components, including a printed circuit board 1291, excitation light sources 1282, an alignment key 1290, an excitation filter 1283, a compression module 1274, an emission filter 1289, photodetectors 1286, a photodetector plate 1287, which are substantially similar to their counterparts in FIG. 11A (i.e., printed circuit board 1191, excitation light sources 1182, alignment key 1190, excitation filter 1183, compression module 1174, emission filter 1189, photodetectors 1186, and photodetector plate 1187).

In the arrangement shown in FIG. 12, the reaction assembly and the optical detection assembly extend in an overlapping longitudinal space. FIG. 12 also conveys that the reaction assembly may be arranged such that it is disposed within certain components of the optical detection assembly. This saving of real estate on the target analyte data collecting device allows for the device to provide functionalities that allow for on-site testing and real time results.

Figure 13:
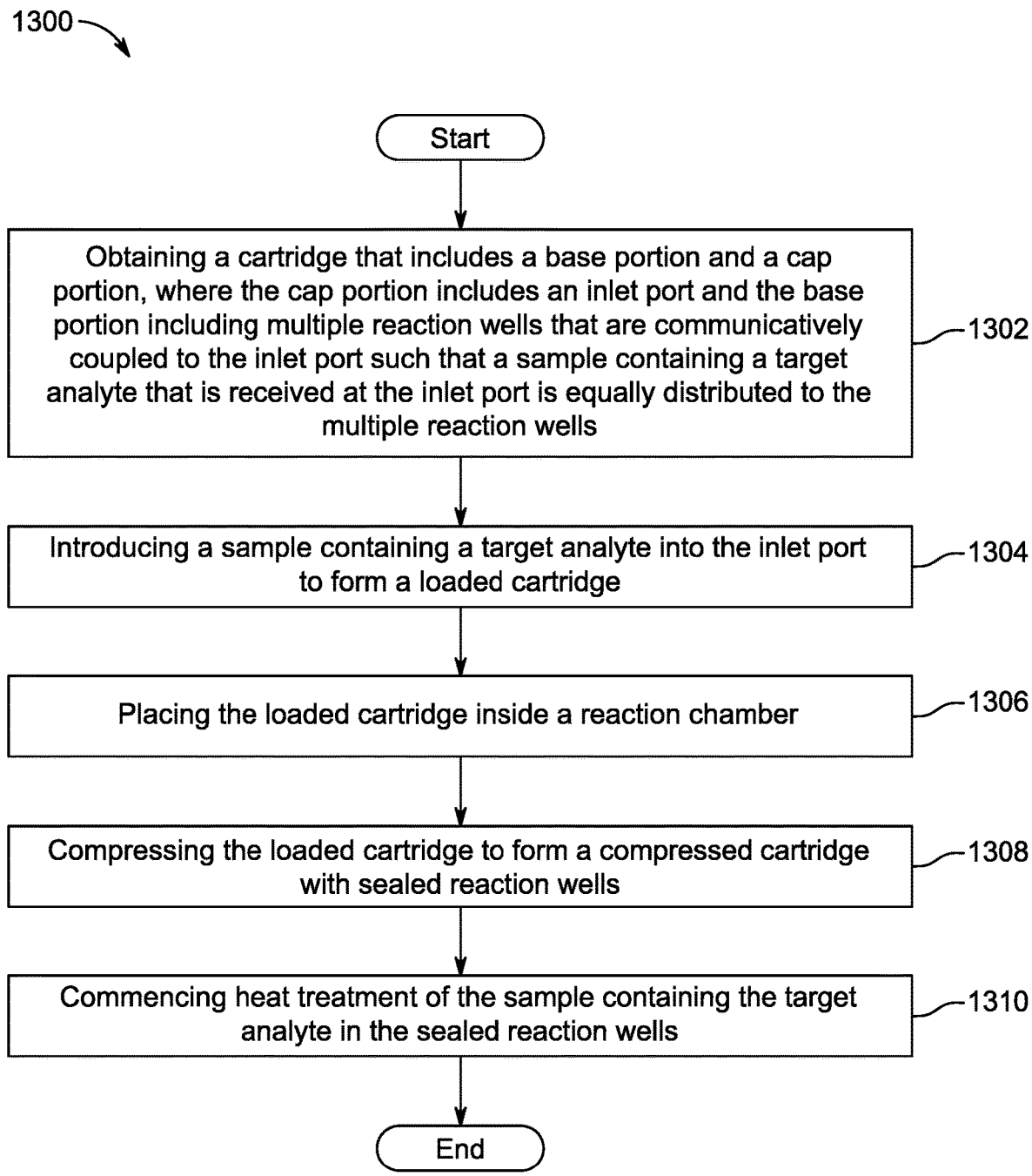
FIG. 13 shows certain salient steps of a method, according one embodiment of the present teachings for detecting a presence and/or a characteristic of a target analyte.
Figure 14:
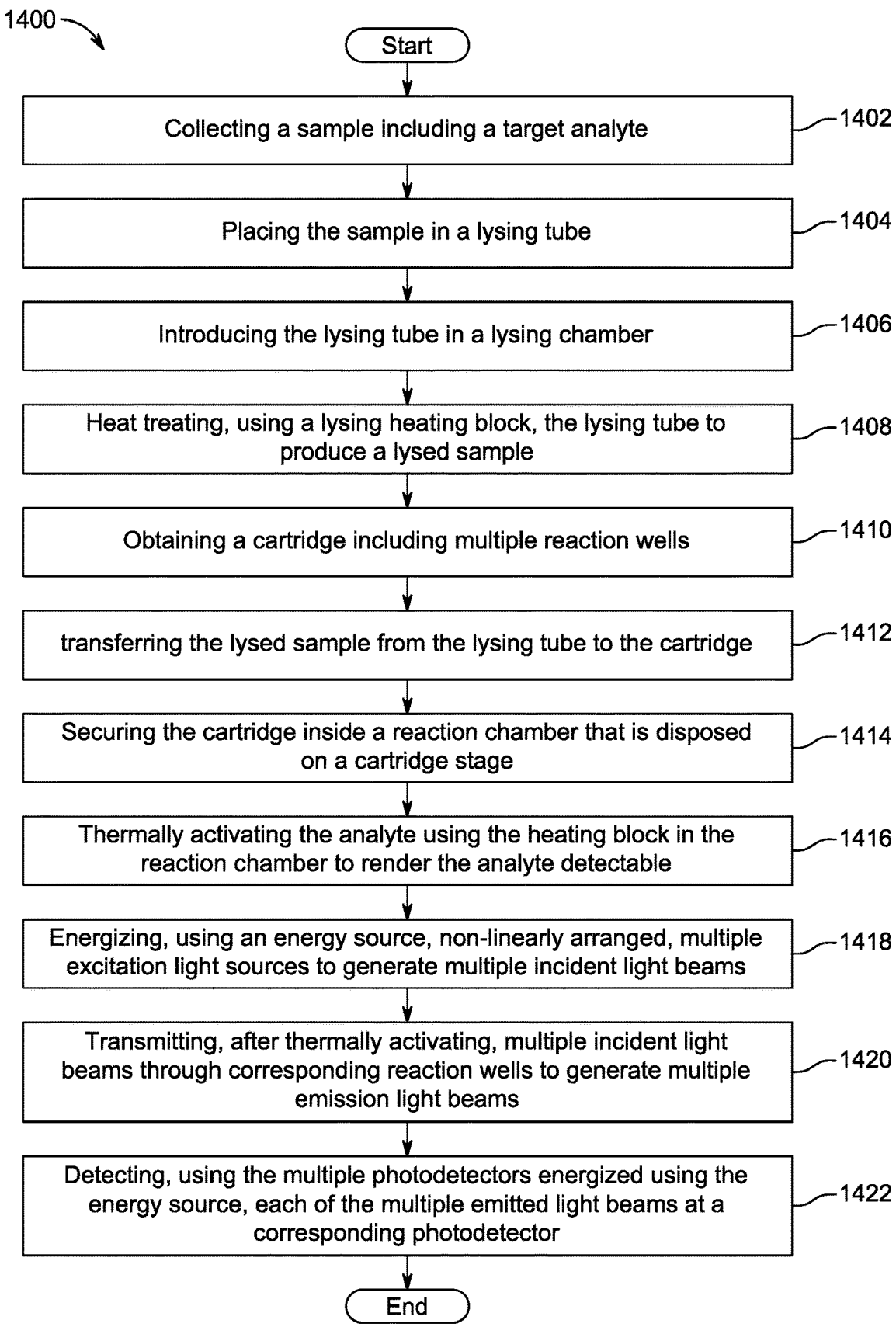
FIG. 14 shows certain salient steps of a method, according to one embodiment of the present teachings, for determining presence and/or a characteristic of a target analyte in a sample.
Figure 15:
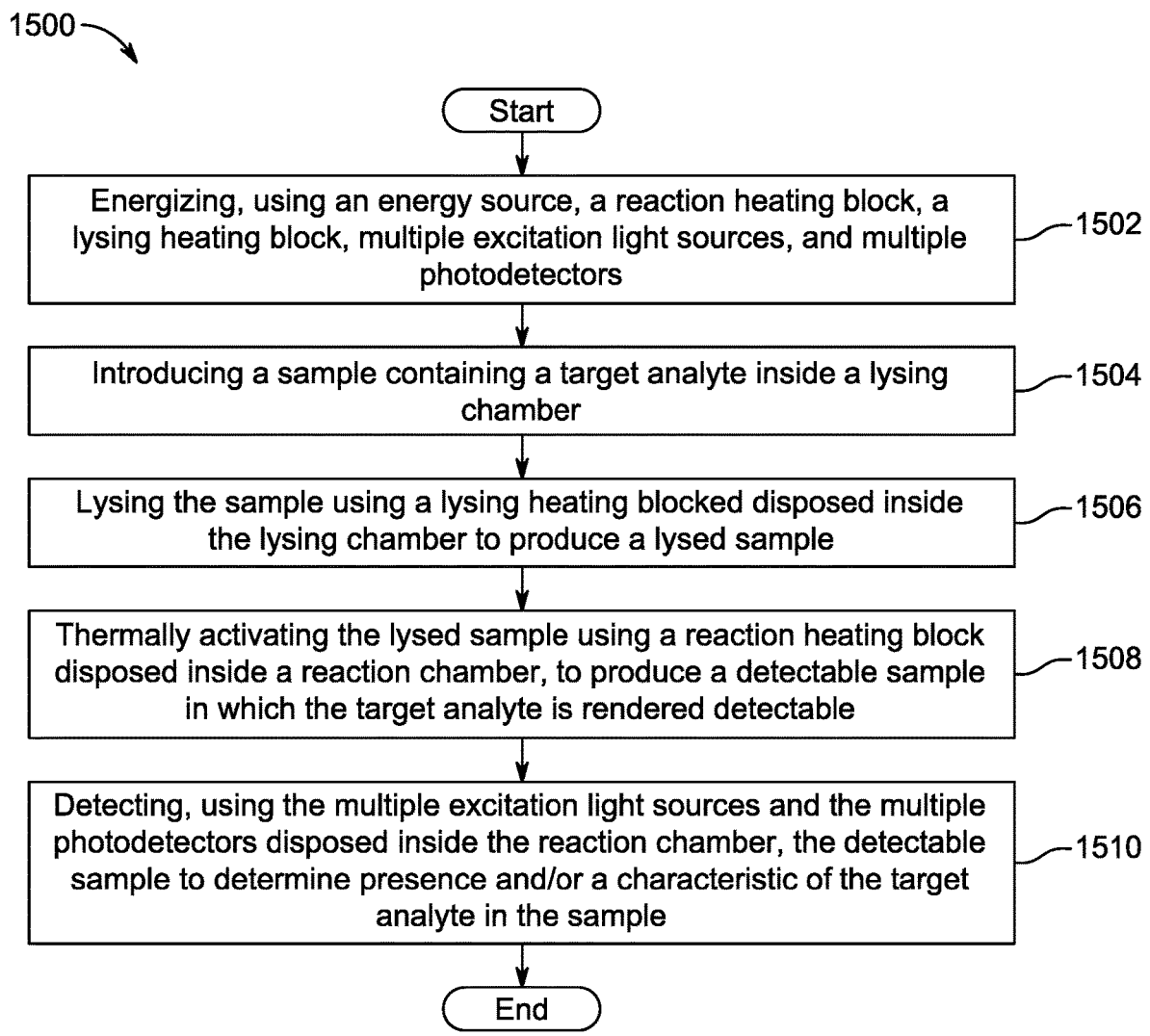
FIG. 15 shows certain salient steps of a collection method, according to one embodiment of the present teachings, for collecting target analyte data.

FIGS. 13-15 describe various methods according to the present teachings. It is not necessary to use the structural details described herein (i.e., details described in connection with FIGS. 1-13) to practice these methods. However, using the structural details described herein to carry out the present methods, as they are described in FIGS. 13-15, represents preferred embodiments of the present teachings.

FIG. 13 is a flowchart of a method of detecting a presence and/or a characteristic of a target analyte 1300, according to one embodiment of the present teachings. Method 1300, preferably, begins with a step 1302 of obtaining a cartridge (e.g., cartridge 531 shown in FIG. 5) including a base portion (e.g., base portion 532 shown in FIG. 5) and a cap portion (e.g., cap portion 533 shown in FIG. 5). In this step, the cap portion includes an inlet port (e.g., inlet port 753 shown in FIG. 7B) and the base portion including multiple reaction wells (e.g., multiple reaction wells 637 shown in FIG. 6B).

Next a step 1304 includes introducing the sample containing the target analyte into the inlet port to form a loaded cartridge. Then, method 1300 proceeds to a step 1306, which includes placing the loaded cartridge in a reaction chamber (e.g., reaction chamber 1010 shown in FIGS. 10A and 10B). Inside the reaction chamber, a next step 1308 is carried out. This step includes compressing the loaded cartridge to form a compressed cartridge such that the multiple reaction wells are sealed from the ambient conditions to form sealed multiple reaction wells. In one embodiment of the present teachings, a compression module (e.g., compression module 1174 shown in FIG. 11A) is used to implement step 1308. Method 1300 then performs a step 1310, which includes commence heat treatment of the sample containing the target analyte in the sealed multiple reaction wells such that no amount to a substantially reduced amount of evaporation of the sample escapes the sealed multiple reaction wells. Step 1310 also transforms the sample including the target analyte into a detectable sample.

In certain preferred implementations of the present teachings, method 1300 further includes a step of equally distributing, which is carried out as part of step 1304, the sample containing the target analyte inside the multiple wells. Method 1300 may further include orienting, prior to performing step 1308, the cartridge using an orientation key (e.g., orientation key 634 shown in FIGS. 6A-6C) disposed on the cartridge. In this step, the orientation key serves as a point of reference that positions each of the multiple reaction wells at a predefined location. In one implementation, the commencing step of the present teachings includes contacting a reaction heating block with the multiple reaction wells. Further, as a result of the orientation step, the multiple reactions wells are in the proper position to undergo heating and/or detecting as described herein.

Method 1300 further, preferably, includes preloading one or more reaction material in the multiple reaction wells to form a pre-loaded cartridge. In this step of preloading, one or more of the reaction materials is at least one member chosen from a group comprising reagent, buffer, and probe. Method 1300 may further include, after the step of preloading, a step of lyophilizing the reaction materials in the multiple reaction wells. The steps of preloading and lyophilizing are preferably carried out prior to obtaining step 1302. As a result, method of detecting a presence and/or a characteristic of a target analyte 1300, if desired may be carried out on-site and real-time results may be obtained. In this embodiment of the present teachings, the need for going to a laboratory is obviated because all the necessary reaction materials for method 1300 are preloaded in the cartridge.

In another aspect, the present teachings provide other methods for determining presence and/or a characteristic of a target analyte in a sample. One such method 1400 is described in FIG. 14 and, preferably, begins with a step 1402, which includes collecting a sample including a target analyte. Next, a step 1404 involves placing the sample in a lysing tube (e.g., lysing tube 104 shown in FIG. 1). Then, in a step 1406, the lysing tube is introduced into the lysing chamber (e.g., lysing chamber 409 shown in FIG. 4A). At this stage of method 1400, lysing tube is prepared for undergoing lysing. To this end, a step 1408 includes heat treating, using a heating block, the lysing tube to produce a lysed sample. The present teachings recognize that steps 1402, 1404, 1406 and 1408 are optional and are carried out in certain preferred embodiments of the present teachings.

According to one preferred embodiment of the present teachings, heat treating in step 1408 maintaining a temperature of the lysing chamber at about 95° C. for about 2 minutes and then at about 65° C. for about 5 minutes. Similar heat treating steps may also be carried out in a reaction chamber in heat treatment performed (e.g., in step 1414, described below).

Regardless of whether steps 1402 to 1408, are implemented, method 1400 includes a step 1410 that includes obtaining a cartridge including multiple reaction wells having contained therein the sample including the target analyte. Step 1410 is substantially similar to step 1302 of FIG. 13. Then, in an optional step 1412, the lysed sample is transferred from the lysing tube (e.g., lysing chamber 409 shown in FIG. 4A) to the cartridge (e.g., cartridge 531 shown in FIG. 5). This transferring step of the present teachings may be carried out using at least one member chosen from a group comprising syringe, pipette, eye dropper, capillary tube, paper strip, and dipstick.

Next, a step 1414 includes securing, inside a reaction chamber (reaction chamber 1010 shown in FIG. 10A), the cartridge disposed on a cartridge stage (e.g., cartridge stage 1070 shown in FIG. 10A). In this step, the cartridge stage has defined therein an opening (e.g., opening 1015 shown in FIG. 10A) such that a cap portion (e.g., cap portion 733 shown in FIG. 7B) is disposed above the opening and the base portion (e.g., base portion 632 shown in FIG. 6B) is disposed below the opening. In this step, the reaction chamber includes a nonlinear-shaped heating block (e.g., circular shaped reaction heating block 964 shown in FIGS. 9A and 9B and reaction heating block 1064 shown in FIG. 10A) disposed inside a housing disposed below the opening. Further, the heating block has defined therein a heating block aperture (e.g., heating block aperture 971 shown in FIGS. 9A and 9B) that includes an inner heating surface (e.g., inner heating surface 965 shown in FIG. 9B) having a curved profile designed to conform to a curved profile of an outer surface of a side portion of the multiple reaction wells. Securing step 1414 may further include establishing direct contact of the inner heating surface with the outer surface of the side portion of the multiple reaction wells (e.g., reaction well 637 shown in FIG. 6B) or multiple reaction housings (e.g., reaction housing 636 shown in FIG. 6A).

As shown in FIG. 14, method 1400 then proceeds a step 1416, which includes thermally activating, using the reaction heat block disposed inside the reaction chamber, the sample including the target analyte to render the sample detectable. By way of example, thermally activating step 1416 is carried out under isothermal conditions.

The analyte, preferably, includes at least one member selected from a group comprising DNA, RNA, and protein. Further, the step of thermally activating may include amplifying the analyte. The analyte may be a severe acute respiratory syndrome coronavirus 2 (Covid-19). In one implementation, the step of thermally activating of the present teachings may include applying one or more different types of energy that is chosen from a group comprising thermal energy, mechanical energy, magnetic energy, electric energy, acoustic energy, radiation energy, and fluidic energy.

Method 1400, similar to method 1300 of FIG. 13, may further still include a step of preloading the cartridge with any one reaction material chosen from a group comprising reagent, buffer and probe to form a preloaded cartridge and to facilitate detection of the analyte. As explained in connection with FIG. 13, after the step of preloading, a step of lyophilizing may be carried out. The steps of preloading and lyophilizing are, preferably, carried out prior to the step of collecting.

Method 1400 may also involve detecting the analyte. To this end, method 1400 may perform a step 1418 of energizing, using an energy source (e.g., a battery installed inside device 100 shown in FIG. 1), non-linearly arranged, multiple excitation light sources (e.g., light sources 1182 shown in FIG. 11A) to generate multiple incident light beams. Next, a step 1420 includes transmitting each of the multiple incident light beams through a corresponding one of the multiple reaction wells (e.g., reaction wells 1137 shown in FIG. 11A) to generate multiple emission light beams. Then, a step 1422 includes detecting, using multiple photodetectors (e.g., photodetectors 1186 of FIG. 11A) energized using the energy source, each of the multiple emitted light beams at a corresponding one of the multiple photodetectors. In this step, each of the multiple excitation light sources corresponds to one of the multiple incident light beams, one of the multiple reaction wells, one of the multiple emission light beams, and one of the multiple photodetectors. In one embodiment of the present teachings, energizing step 1418 does not energize a cooling mechanism on device 100 of FIG. 1 to effect isothermal reactions either in the lysing chamber or in the reaction chamber.

The step of detection may be in carried out according many different implementations. In one implementation of the present teachings, the detecting step includes detecting an emission signal generated by a probe. By way of example, the step of detecting an emission signal includes translating the emission signal, using an algorithm, to produce a result that is displayed at a user interface (e.g., user interface 211 shown in FIG. 2). As another example, the step of detecting the emission signal includes detecting a signature that is at least one member selected from a group comprising optical signature, electrochemical signature, magnetic signature, and mechanical signature.

The step of detecting may include detecting presence of the analyte in a biomolecule sample. In this embodiment, the above-mentioned step of the obtaining includes collecting a sample from of at least one member chosen from a group comprising virus, microbe, bacteria, water, food, beverage, soil, plant, oil, animal tissue, animal byproduct, air, filter of air or water, and item that has contacted food.

FIG. 15 shows a flowchart for a method of collecting target analyte data 1500, according to one embodiment of the present teachings. Method 1500, preferably, begins with a step 1502 that includes energizing, using an energy source, a reaction heating block, a lysing heating block, multiple excitation light sources and multiple photodetectors. Then, a step 1504 includes introducing a sample containing a target analyte inside a lysing chamber (which includes the lysing heating block).

Method 1500 then proceeds to a step 1506, which includes lysing, using the lysing heating blocked disposed inside the lysing chamber, the sample to produce a lysed sample. By way of example, lysing heating block 425 shown in FIG. 4A includes a receiving surface (which is designed to receive lysing tube 404 shown in FIG. 4A) having a shape that conforms to the shape of the outer surface of lysing tube 104. As a result, the lysing heating block effectively lyses the sample to produce a lysed sample.

Next, a step 1508 includes thermally activating, using the reaction heating block disposed inside a reaction chamber (e.g., circular shaped reaction heating block 964 shown in FIGS. 9A and 9B and reaction heating block 1064 shown in FIG. 10A), the lysed sample to produce a detectable sample in which the target analyte is rendered detectable. After thermal activation is performed to obtain a detectable sample, a step 1510 is performed. Step 1510 includes detecting, using the multiple excitation light sources and the multiple photodetectors disposed inside the reaction chamber, the detectable sample to determine presence and/or a characteristic of the target analyte in the sample.

Method 1500 may further include a step of transferring the lysed sample to the reaction chamber containing the reaction heating block. The steps of lysing and/or the thermally activating, preferably, include applying one or more different types of energy that is chosen from a group comprising thermal energy, mechanical energy, magnetic energy, electric energy, acoustic energy, radiation energy, and fluidic energy. The step of detecting includes detecting an optical signal generated by a probe and determines an amount of the target analyte present in the sample.

The systems and methods of the present arrangements and teachings recognize the need for sample testing that may be carried in the field by non-experts in a manner that provides quick and accurate results, and in particular, determining presence and/or characteristics of one or more target analytes in a sample. By way of example, such sample testing may include but is not limited to, quantitative PCR analysis of target DNA in biosamples for purposes of species identification. The systems and methods of the present teachings, however, are not intended to be limited to biosamples testing, nor are they confined to amplification reactions or isothermal reactions, and instead contemplate testing of any sample containing one or more target analytes that are capable of being tested according to the systems and arrangements of the present inventions, using any method known to those of skill in the art. By way of non-limiting example, a sample to be tested for the presence and/or characteristics of one or more target analytes according to the systems and methods of the present inventions may include a food, a beverage, a soil sample, a plant sample, an oil sample, a sample of animal tissue, a sample from an animal byproduct, an air sample, a sample from a filter of air or water, a virus sample, a microbe sample, a bacteria sample, and a water sample, an oil sample, a dairy sample, a wine sample, or a sample that has contacted food, beverages, water, plants, or animals.

Likewise, such diagnostic testing using the devices of the present invention may include, but are not limited to, heavy metal testing, immunoassays and enzyme linked immunosorbent assays, hormone tests, lipid panels, and antibiotic tests. Unlike conventional systems, which carry out such testing in laboratory settings, the present inventions relate to systems and methods that allow for carrying out such testing in the field, via a single, hand-held device that integrates a sample preparation chamber and a reaction/detection chamber and that includes components (e.g., a user interface and computer) that serve to facilitate ease of use by a non-user. Further, the systems and methods of the present teachings implement a novel system that provides for closed-feedback control of temperature in the sample-preparation chamber and/or the reaction/detection chamber.

It is also noteworthy that because certain reactions in a lysing chamber and/or a reaction may be automated via connection of each chamber to various components, such as a heater (e.g., a resistive heater), a cooler (e.g., a thermoelectric cooler), a temperature sensor, a computer, and/or user interface, a non-expert user in the field may carry out these steps so long as the user is capable of simply collecting and/or introducing a collected sample into the system, and transferring a treated or processed sample from a sample-processing (e.g., lysing) chamber to a reaction. Such features facilitate ease of use such that a non-expert end-user may practice the present teachings and produce results in the field.

Although illustrative embodiments of the present arrangements and teachings have been shown and described, other modifications, changes, and substitutions are intended. Accordingly, it is appropriate that the appended claims be construed broadly and in a manner consistent with the scope of the disclosure, as set forth in the following claims.

What is claimed is:

1. A cartridge for providing a target analyte for detection, said cartridge comprising:
    a base portion including:
        a receiving area located at a center region of said base portion, wherein said base portion has a circular shape;
        multiple reaction wells radially disposed near a perimeter of said base portion, wherein said receiving area is a surface that is raised relative to said multiple reaction wells; and
        multiple connecting tracks that substantially linearly extend from a region at or proximate to said receiving area to said multiple reaction wells and designed to convey a sample including said target analyte from said receiving area to said multiple reaction wells, such that one end of each of said connecting tracks is fluidly connected to said receiving area and another end of each of said connecting tracks is fluidly connected to each of said multiple reaction wells; and
    a cap portion including:
        an inlet port located at a center cap region of said cap portion;
        multiple reaction well covers radially disposed near a perimeter of said cap portion;
        multiple connecting track covers that extend from said inlet port to said multiple reaction well covers;
        multiple vents designed to regulate flow of said sample into said multiple reaction wells;
        wherein said cap portion has a circular shape; and
        wherein in an assembled state of said cartridge, said inlet port covers said receiving area, said multiple reaction well covers cover said multiple reaction wells, and said multiple connecting track covers cover said multiple connecting tracks to define an enclosed fluid flow path for said sample.

2. The cartridge for providing a target analyte for detection of claim 1, wherein said base portion further comprises multiple securing features that extend from said perimeter of said base portion and each of which includes an overhanging portion that is designed to secure onto an edge of said cap portion, such that said cap portion is effectively secured to said base portion.

3. The cartridge for providing a target analyte for detection of claim 1, wherein said base portion further includes a supporting feature that is raised relative to said multiple reaction wells, and having disposed thereon said receiving area and multiple channel dividers radially disposed around said receiving area such that multiple channel entry regions linearly extend between adjacent said multiple channel dividers into said multiple connecting tracks for receiving said sample received at said receiving area.

4. The cartridge for providing a target analyte for detection of claim 1, wherein a cross-sectional area of each of said multiple vents ranges from about 0.01 mm$^2$ to about 0.25 mm$^2$.

5. The cartridge for providing a target analyte for detection of claim 2, wherein said base portion further includes multiple reaction well housings, each of which includes:
    one of said multiple reaction wells,
    a first compression resisting region, and
    a second compression resisting region,
    wherein said cap portion further includes multiple reaction well housing covers, each of which includes:
    said multiple reaction well covers, and
    a first compression region, and
    wherein each of said multiple connecting track covers includes a second compression region,
    wherein said first compression region is a recessed area on one end of each of said multiple reaction well covers and said second compression region is a recessed area on another end of each of said multiple reaction well covers, and
    wherein each of said first compression resisting region and said second compression resisting region is a region on said base portion that is rigid relative to said first compression region and said second compression region, and each of said first compression region and said second compression region is compressible relative to each of said first compression resisting region and said second compression resisting region, such that in an assembled state of said base portion and said cap portion, said first compression region compresses against said first compression resisting region to form a first seal and said second compression region compresses against said second compression resisting region to form a second seal, such that in a compressed state of said cartridge, said first seal and said second seal effectively seal off said multiple reaction wells from ambient conditions.

6. The cartridge for providing a target analyte for detection of claim 5, further comprising a third compression region disposed on said inlet port, wherein said third compression resisting region is rigid relative to said third compression region, and said third compression region is compressible relative to said third compression resisting region, such that in a compressed state of said compression region, said third compression region compresses against said third compression resisting region, such that said inlet port is sealed from ambient conditions.

7. The cartridge for providing a target analyte for detection of claim 5, wherein said first seal seals off one or more vents configured on said cap portion and that are designed to regulate flow of said sample into said multiple reaction wells such that said first seal prevents flow inside and/or outside one of said multiple reaction wells.

8. The cartridge for providing a target analyte for detection of claim 5, wherein a base portion flow path extends linearly from said receiving area to each of said multiple channel entry region to one of said multiple connecting tracks and from one of said multiple connecting tracks to one of said multiple reaction wells, wherein one of said includes one of said multiple second compression resisting regions.

9. The cartridge for providing a target analyte for detection of claim 1, wherein said inlet port has a diameter that ranges from about 3.5 mm to about 3.8 mm.

10. The cartridge for providing a target analyte for detection of claim 1, wherein one dimension of said inlet port ranges from about 1 mm to about 5 mm.

11. The cartridge for providing a target analyte for detection of claim 1, wherein one of said multiple reaction wells has a volume that ranges from about 5 microliters to about 100 microliters.

12. The cartridge for providing a target analyte for detection of claim 1, wherein said multiple reaction wells are non-linearly arranged outside said receiving portion.

13. The cartridge for providing a target analyte for detection of claim 1, wherein said multiple reaction wells are arranged in a circular configuration along said perimeter of said base portion.

14. The cartridge for providing a target analyte for detection of claim 13, wherein one of said multiple reaction wells has a diameter that ranges from about 1 mm to about 4 mm.

15. The cartridge for providing a target analyte for detection of claim 1, wherein said base portion and/or said cap portion are made from an optically transparent material such that said optically transparent material allows for interrogation of optical signals, and wherein said base portion is made from a rigid material and said cap portion is made from a compressible material, such that said rigid material is rigid relative to said compressible material and maintains a high dimensional tolerance, and said compressible material is compressible relative to said rigid material.

16. The cartridge for providing a target analyte for detection of claim 3, further comprising multiple sidewalls, each of which extends from said base portion to said cap portion, such that said multiple sidewalls, said multiple connecting tracks and said multiple connecting track covers integrate to define multiple channels, each of which linearly extends, and thereby provides an enclosed flow path, from one of said multiple channel dividers to one of said multiple reaction wells.

17. The cartridge for providing a target analyte for detection of claim 16, wherein a length of one of said channels linearly extends by a distance that ranges from about 2 mm to about 12 mm.

* * * * *